(12) United States Patent
Souter et al.

(10) Patent No.: US 7,790,666 B2
(45) Date of Patent: Sep. 7, 2010

(54) DETERGENT COMPOSITIONS

(75) Inventors: Philip Frank Souter, Northumberland (GB); John Allen Burdis, New Castle upon Tyne (GB); Neil Joseph Lant, Newcastle upon Tyne (GB)

(73) Assignee: The Procter & Gamble Company, Cincinnati, OH (US)

( * ) Notice: Subject to any disclaimer, the term of this patent is extended or adjusted under 35 U.S.C. 154(b) by 605 days.

(21) Appl. No.: 11/656,263

(22) Filed: Jan. 22, 2007

(65) Prior Publication Data

US 2007/0179075 A1 Aug. 2, 2007

Related U.S. Application Data

(60) Provisional application No. 60/761,188, filed on Jan. 23, 2006, provisional application No. 60/796,267, filed on Apr. 28, 2006, provisional application No. 60/854,787, filed on Oct. 27, 2006.

(51) Int. Cl.
*C11D 17/00* (2006.01)
*C12N 9/20* (2006.01)

(52) U.S. Cl. ..................... 510/419; 510/276; 435/198

(58) Field of Classification Search .............. 510/419, 510/276; 435/198
See application file for complete search history.

(56) References Cited

U.S. PATENT DOCUMENTS

| | | | |
|---|---|---|---|
| 4,430,243 A | 2/1984 | Bragg | |
| 4,597,898 A | 7/1986 | Vander Meer | |
| 4,762,636 A | 8/1988 | Balliello et al. | |
| 4,990,280 A | 2/1991 | Thorengaard et al. | |
| 5,486,303 A | 1/1996 | Capeci et al. | |
| 5,489,392 A | 2/1996 | Capeci et al. | |
| 5,516,448 A | 5/1996 | Capeci et al. | |
| 5,565,422 A | 10/1996 | Del Greco et al. | |
| 5,569,645 A | 10/1996 | Dinniwell et al. | |
| 5,574,005 A | 11/1996 | Welch et al. | |
| 5,576,282 A | 11/1996 | Miracle et al. | |
| 5,595,967 A | 1/1997 | Miracle et al. | |
| 5,597,936 A | 1/1997 | Perkins et al. | |
| 5,691,297 A | 11/1997 | Nassano et al. | |
| 5,879,584 A | 3/1999 | Bianchetti et al. | |
| 6,020,303 A | 2/2000 | Cripe et al. | |
| 6,060,443 A | 5/2000 | Cripe et al. | |
| 6,225,464 B1 | 5/2001 | Hiler, II et al. | |
| 6,291,412 B1 | 9/2001 | Kvita et al. | |
| 6,306,812 B1 | 10/2001 | Perkins et al. | |
| 6,326,348 B1 | 12/2001 | Vinson et al. | |
| 6,495,357 B1 | 12/2002 | Fuglsang et al. | |
| 6,939,702 B1 * | 9/2005 | Vind et al. ................. 435/198 |
| 7,172,997 B2 * | 2/2007 | Minning et al. ............ 510/226 |
| 7,208,459 B2 * | 4/2007 | Sadlowski et al. .......... 510/419 |
| 2003/0087790 A1 | 5/2003 | Fuglsang et al. | |
| 2003/0087791 A1 | 5/2003 | Bonelli et al. | |
| 2004/0048764 A1 | 3/2004 | Kim et al. | |
| 2005/0003983 A1 | 1/2005 | Kim et al. | |
| 2005/0059130 A1 | 3/2005 | Bojsen et al. | |
| 2005/0227891 A1 | 10/2005 | Dreyer et al. | |

FOREIGN PATENT DOCUMENTS

| | | |
|---|---|---|
| EP | 0 851 913 B1 | 5/2004 |
| EP | 1 555 322 A1 | 7/2005 |
| WO | WO 92/05249 A1 | 4/1992 |
| WO | WO 94/25577 A1 | 11/1994 |
| WO | WO 95/22615 A1 | 2/1995 |
| WO | WO 97/04079 A1 | 2/1997 |
| WO | WO 97/07202 A1 | 2/1997 |
| WO | WO 98/17767 A1 | 4/1998 |
| WO | WO 99/51714 A2 | 10/1999 |
| WO | WO 00/32601 A2 | 6/2000 |
| WO | WO 00/60063 A1 | 10/2000 |
| WO | WO 01/05874 A1 | 1/2001 |
| WO | WO 02/42740 A1 | 5/2002 |
| WO | WO 03/060112 A1 | 7/2003 |
| WO | WO 2005/042532 A1 | 5/2005 |

\* cited by examiner

*Primary Examiner*—Tekchand Saidha
(74) *Attorney, Agent, or Firm*—James F. McBride; Leonard W. Lewis; Steven W. Miller

(57) ABSTRACT

This invention relates to compositions comprising certain lipase variants and a fabric hueing agent and processes for making and using such compositions. Including the use of such compositions to clean and/or treat a situs.

28 Claims, 3 Drawing Sheets

Figure 1A

```
ID NO 1:    SSSSTQDYRIASEAEIKAHTFYTALSANA
ID NO 2:    SSSSTQDYRIASEAEIKAHTFYTALSANA
ID NO 3:    SIDGGIRAATSQEINELTYYTTLSANS
ID NO 4:    SASDGGKVVAATTAQIQEFTKYAGIAATA
ID NO 5:    TAGHALAASTQ GISEDLYSRL VEMATISQAA
ID NO 6:    TAGHALAASTQ GISEDLYSRL VEMATISQAA
ID NO 7:    AVGVTTTDFSNFKFYIQHGAAA
ID NO 8:    TVTTQDLSNFRFYLQHADAA
ID NO 9:    DIPTTQLEDFKFWVQYAAAT
ID NO 10:   DVSTSELDQFEFWVQYAAAS
ID NO 11:   SVSTSTLDELQLFAQWSAAA
ID NO 12:   SVSTSTLDELQLFSQWSAAA
ID NO 13:   DVSSSLLNNLDLFAQYSAAA
ID NO 14:   EVSQDLFNQFNLFAQYSAAA
ID NO 15:   PQDAYTASHADLVKYATYAGLA

ID NO 1:    YCRTVIPG    GRWSCPHCGVAS   NLQITKTFST   LITDTNVLVAV
ID NO 2:    YCRTVIPG    GQWSCPHCDVAP   NLNITKTFTT   LITDTNVLVAV
ID NO 3:    YCRTVIPG    ATWDCIHCDATE   DLKIIKTWST   LIYDTNAMVAR
ID NO 4:    YCRSVVPG    NKWDCVQCQKWVP  DGKIITTFTS   LLSDTNGYVLR
ID NO 5:    YADLCNIPST                 IIKGEKIYNSQTDINGWILR
ID NO 6:    YADLCNIPST                 IIKGEKIYNSQTDINGWILR
ID NO 7:    YC NSEAAA GSKITCSNNGCPTVQGNGATIVTSF   VGSKTGIGGYVAT
ID NO 8:    YC NFNTAV GKPVHCSAGNCPDIEKDAAIVVGSV   VGTKTGIGAYVAT
ID NO 9:    YCPNNYVAKD GEKLNCSVGNCPDVEAAGSTVKLSFS  DDTITDTAGFVAV
ID NO 10:   YYEADYTAQV GDKLSCSKGNCPEVEATGATVSYDFS  DSTITDTAGYIAV
ID NO 11:   YCSNNID SK DSNLTCTANACPSVEEASTTMLLEFDLTNDFGGTAGFLAA
ID NO 12:   YCSNNID SD DSNVTCTADACPSVEEASTKMLLEFDLTNNFGGTAGFLAA
ID NO 13:   YCDENLN ST GTKLTCSVGNCPLVEAASTQSLDEFNESSSYGNPAGYLAA
ID NO 14:   YCGKNNDAPA GTNITCTGNACPEVEKADATFLYSFE  DSGVGDVTGFLAL
ID NO 15:   YQTTDAWPAS             RTVPKDTTLISSFD  HTLKGSSGYIAF

ID NO 1:    GEKEKTIYVV  FRGTSSIRNA  IADIVFVPVN  YPPV  NGA  KVHKGFLDSY
ID NO 2:    GENEKTIYVV  FRGTSSIRNA  IADIVFVPVN  YPPV  NGA  KVHKGFLDSY
ID NO 3:    GDSEKTIYIV  FRGSSSIRNW  IADLTFVPVS  YPPV  SGT  KVHKGFLDSY
ID NO 4:    SDKQKTIYLV  FRGTNSFRSA  ITDIVFNFSD  YKPV  KGA  KVHAGFLSSY
ID NO 5:    DDSSKEIITV  FRGTGSDTNL  QLDTNYTLTP  FDTLPQCNGC  EVHGGYYIGW
ID NO 6:    DDSSKEIITV  FRGTGSDTNL  QLDTNYTLTP  FDTLPQCNSC  EVHGGYYIGW
ID NO 7:    DSARKEIVVS  FRGSINIRNW  LTNLDFG QE  DCSL  VSGC  GVHSGFQRAW
ID NO 8:    DNARKEIVVS  VRGSINVRNW  ITNFNFG QK  TCDL  VAGC  GVHTGFLDAW
ID NO 9:    DNTNKAIVVA  FRGSYSIRNW  VTDATFP QT  DPGL  CDGC  KAELGFWTAW
ID NO 10:   DHTNSAVVLA  FRGSYSVRNW  VADATFV HT  NPGL  CDGC  LAELGFWSSW
ID NO 11:   DNTNKRLVVA  FRGSSTIENW  IANLDFILED  NDDL  CTGC  KVHTGFWKAW
ID NO 12:   DNTNKRLVVA  FRGSSTIKNW  IADLDFILQD  NDDL  CTGC  KVHTGFWKAW
ID NO 13:   DETNKLLVLS  FRGSADLANW  VANLNFGLED  ASDL  CSGC  EVHSGFWKAW
ID NO 14:   DNTNKLIVLS  FRGSRSIENW  IGNLNFDLKE  INDI  CSGC  RGHDGFTSSW
ID NO 15:   NEPCKEIIVA  YRGTDSLIDW  LTNLNFDKTA  WPAN  ISNS  LVHEGFLNAY

ID NO 1:    NEVQDKLVAE  VKAQLDRHPG  YKIVVTGHSL  GGATAVLSALDLYHHGHA
ID NO 2:    NEVQDKLVAE  VKAQLDRHPG  YKIVVTGHSL  GGATAVLSALDLYHHGHD
ID NO 3:    GEVQNELVAT  VLDQFKQYPS  YKVAVTGHSL  GGATALLCALDLYQREEGLS
ID NO 4:    EQVVNDYFPV  VQEQLTAHPT  YKVIVTGHSL  GGAQALLAGMDLYQREPRLS
ID NO 5:    VSVQDQVESL  VKQQVSQYPD  YALTVTGHSL  GASLAALTAAQL SATYD
ID NO 6:    ISVQDQVESL  VQQQVSQFPD  YALTVTGHSL  GASLAALTAAQL SATYD
ID NO 7:    NEISSQATAA  VASARKANPS  FNVISTGHSL  GGAVAVLAAANLRVGGT
ID NO 8:    EEVAANVKAA  VSAAKTANPT  FKFVVTGHSL  GGAVATIAAAYLRKDGF
ID NO 9:    KVVRDRIIKT  LDELKPEHSD  YKIVVGHSL   GGAIASLAAADLRTKNY
ID NO 10:   KLVRDDIIKE  LKEVVAQNPN  YELVVVGHSL  GAAVATLAATDLRGKGYP
ID NO 11:   ESAADELTSK  IKSAMSTYSG  YTLYFTGHSL  GGALATLGATVLRNDGY
ID NO 12:   EAAADNLTSK  IKSAMSTYSG  YTLYFTGHSL  GGALATLGATVLRNDGY
ID NO 13:   SEIADTITSK  VESALSDHSD  YSLVLTGHSY  GAALAALAATALRNSGH
```

Figure 1B

```
ID NO 14:   RSVADTLRQK VEDAVREHPD YRVVFTGHSL GGALATVAGADLRGNGY
ID NO 15:   LVSMQQVQEA VDSLLAKCPD ATISFTGHSL GGALACISMVDTAQRHRGI

ID NO 1:    NIEIYTQG QPRIGTPAFA NYVIGT      KIPYQRLVHERDIVPHL
ID NO 2:    NIEIYTQG QPRIGTPEFA NYVIGT      KIPYQRLVNERDIVPHL
ID NO 3:    SSNLFLYTQG QPRVGDPAFA NYVVST    GIPYRRTVNERDIVPHL
ID NO 4:    PKNLSIFTVG GPRVGNPTFA YYVEST    GIPFQRTVHKRDIVPHV
ID NO 5:    NIRLYTFG EPRSGNQAFA SYMNDAFQASSPDTTQYFRVTHANDGIPNL
ID NO 6:    NIRLYTFG EPRS NQAFA SYMNDAFQASSPDTTQYFRVTHANDGIPNL
ID NO 7:    PVDIYTYG SPRVGNAQLS AFVSNQ      AGGEYRVTHADDPVPRL
ID NO 8:    PFDLYTYG SPRVGNDFPA NFVTQQ      TGAEYRVTHGDDPVPRL
ID NO 9:    DAILYAYA APRVANKPLA EFITNQ      GNNYRFTHNDDPVPKL
ID NO 10:   SAKLYAYA SPRVGNAALA KYITAQ      GNNFRFTHTNDPVPKL
ID NO 11:   SVELYTYG CPRIGNYALA EHITSQ      GSGANFRVTHLNDIVPRV
ID NO 12:   SVELYTYG CPRVGNYALA EHITSQ      GSGANFPVTHLNDIVPRV
ID NO 13:   SVELYNYG QPRLGNEALA TYITDQ      NKGGNYRVTHTNDIVPKL
ID NO 14:   DIDVFSYG APRVGNRAFA EFLTVQ      TGGTLYRITHTNDIVPRL
ID NO 15:   KMQMFTYG QPRTGNQAFA EYVENL      GHPVFRVVYRHDIVPRM

ID NO 1:    PPGAFGFLHA GEEFWIMK            DSSLRVCPNGIETDNCSNSIV
ID NO 2:    PPGAFGFLHA GEEFWIMK            DSSLRVCPNGIETDNCSNSIV
ID NO 3:    PPAAFGFLHA GEEYWITD            NSPETVQVCTSDLETSDCSNSIV
ID NO 4:    PPQSFGFLHP GVESWIKS            GTSNVQICTSEIETKDCSNSIV
ID NO 5:    PPVEQGYAHG GVEYWSV             DPYSAQNTFVCTGDEVQCCE AQGGQG
ID NO 6:    PPADEGYAHG VVEYWSV             DPYSAQNTFVCTGDEVQCCE AQGGQG
ID NO 7:    PPLIFGYRHT TPEFWLSGGGGDKVDYTISDVKVCEGAANLG CNGGTL
ID NO 8:    PPIVFGYRHT SPEYWLNG GPLDKDYTVTEIKVCEGIANVM CNGGTI
ID NO 9:    PLLTMGYVHI SPEYYITA PDNTTVTDNQVTVLDGYVNFK GNTGTS
ID NO 10:   PLLSMGYVHV SPEYWITS PNNATVSTSDIKVIDGDVSFD GNTGTG
ID NO 11:   PPMDFGFSQP SPEYWITS GNGASVTASDIEVIEGINSTA GNAGEA
ID NO 12:   PPMDFGFSQP SPEYWITS GTGASVTASDIELIEGINSTA GNAGEA
ID NO 13:   PPTLLGYHHF SPEYYISS ADEATVTTTDVTEVTGIDATG GNDGTD
ID NO 14:   PPREFGYSHS SPEYWIKS GTLVPVTRNDIVKIEGIDATG GNNQPN
ID NO 15:   PPMDLGFQHH GQEVWYEG            DENIKFCKGEGENLTCELGVP

ID NO 1:    PFT    SVIDHLSYLDMNTGL CL
ID NO 2:    PFT    SVIDHLSYLDMNTGL CL
ID NO 3:    PFT    SVLDHLSYFGINTGL CT
ID NO 4:    PFT    SILDHLSYFDINEGS CL
ID NO 5:    VN     NAHTTYF GMTSGACTW
ID NO 6:    VN     NAHTTYF GMTSGHCTW
ID NO 7:    GL     DIAAHLHYF QATDA CNAGGFSWR R
ID NO 8:    GL     DILAHITYF QSMAT CAPIAIPWK R
ID NO 9:    GGLPDLLAFHSHVWYFIHADACKGPGLPLR
ID NO 10:   LPLLTDFEAHIWYF VQVDA GKGPGLPFK R
ID NO 11:   TV     SVLAHLWYF FAISE CLL
ID NO 12:   TV     DVLAHLWYF FAISE CLL
ID NO 13:   GT     SIDAHRWYF IYISE CS
ID NO 14:   IP     DIPAHLWYF GLIGT CL
ID NO 15:   FSEL NAKDHSEYP GMH
```

| ID NO: | Micro organism | SEQ ID NO.: |
|---|---|---|
| 1. | *Absidia reflexa* | 3 |
| 2. | *Absidia corymbifera* | 4 |
| 3. | *Rhizmucor miehei* | 5 |
| 4. | *Rhizopus delemar (oryzea)* | 6 |
| 5. | *Aspergillus niger* | 7 |
| 6. | *Aspergillus tubingensis* | 8 |
| 7. | *Fusarium oxysporum* | 9 |
| 8. | *Fusarium heterosporum* | 10 |
| 9. | *Aspergillus oryzae* | 11 |
| 10. | *Penicilium camembertii* | 12 |

Figure 1C

| | | |
|---|---|---|
| 11. | *Aspergillus foetidus* | 13 |
| 12 | *Aspergillus niger* | 14 |
| 13. | *Aspergillus oryzea* | 15 |
| 14. | *Thermomyces lanuginosus* | 2 |
| 15. | *Landerina penisapora* | 16 |

Figure 1. Alignment of lipase sequences.

```
                           SEQUENCE LISTING

<160> NUMBER OF SEQ ID NOS: 16

<210> SEQ ID NO 1
<211> LENGTH: 807
<212> TYPE: DNA
<213> ORGANISM: Thermomyces lanuginosus
<220> FEATURE:
<221> NAME/KEY: CDS
<222> LOCATION: (1)..(807)
<220> FEATURE:
<221> NAME/KEY: mat_peptide
<222> LOCATION: (1)..()

<400> SEQUENCE: 1 gag gtc tcg cag gat ctg ttt aac cag ttc aat ctc ttt gca cag tat      48
Glu Val Ser Gln Asp Leu Phe Asn Gln Phe Asn Leu Phe Ala Gln Tyr
1               5                   10                  15 tct gca gcc gca tac tgc gga aaa aac aat gat gcc cca gct ggt aca      96
Ser Ala Ala Ala Tyr Cys Gly Lys Asn Asn Asp Ala Pro Ala Gly Thr
                20                  25                  30 aac att acg tgc acg gga aat gcc tgc ccc gag gta gag aag gcg gat     144
Asn Ile Thr Cys Thr Gly Asn Ala Cys Pro Glu Val Glu Lys Ala Asp
            35                  40                  45 gca acg ttt ctc tac tcg ttt gaa gac tct gga gtg ggc gat gtc acc     192
Ala Thr Phe Leu Tyr Ser Phe Glu Asp Ser Gly Val Gly Asp Val Thr
        50                  55                  60 ggc ttc ctt gct ctc gac aac acg aac aaa ttg atc gtc ctc tct ttc     240
Gly Phe Leu Ala Leu Asp Asn Thr Asn Lys Leu Ile Val Leu Ser Phe
65                  70                  75                  80 cgt ggc tct cgt tcc ata gag aac tgg atc ggg aat ctt aac ttc gac     288
Arg Gly Ser Arg Ser Ile Glu Asn Trp Ile Gly Asn Leu Asn Phe Asp
                85                  90                  95 ttg aaa gaa ata aat gac att tgc tcc ggc tgc agg gga cat gac ggc     336
```

-continued

```
Leu Lys Glu Ile Asn Asp Ile Cys Ser Gly Cys Arg Gly His Asp Gly
                100                 105                 110 ttc act tcg tcc tgg agg tct gta gcc gat acg tta agg cag aag gtg      384
Phe Thr Ser Ser Trp Arg Ser Val Ala Asp Thr Leu Arg Gln Lys Val
            115                 120                 125 gag gat gct gtg agg gag cat ccc gac tat cgc gtg gtg ttt acc gga      432
Glu Asp Ala Val Arg Glu His Pro Asp Tyr Arg Val Val Phe Thr Gly
    130                 135                 140 cat agc ttg ggt ggt gca ttg gca act gtt gcc gga gca gac ctg cgt      480
His Ser Leu Gly Gly Ala Leu Ala Thr Val Ala Gly Ala Asp Leu Arg
145                 150                 155                 160 gga aat ggg tat gat atc gac gtg ttt tca tat ggc gcc ccc cga gtc      528
Gly Asn Gly Tyr Asp Ile Asp Val Phe Ser Tyr Gly Ala Pro Arg Val
                165                 170                 175 gga aac agg gct ttt gca gaa ttc ctg acc gta cag acc ggc gga aca      576
Gly Asn Arg Ala Phe Ala Glu Phe Leu Thr Val Gln Thr Gly Gly Thr
            180                 185                 190 ctc tac cgc att acc cac acc aat gat att gtc cct aga ctc ccg ccg      624
Leu Tyr Arg Ile Thr His Thr Asn Asp Ile Val Pro Arg Leu Pro Pro
    195                 200                 205 cgc gaa ttc ggt tac agc cat tct agc cca gag tac tgg atc aaa tct      672
Arg Glu Phe Gly Tyr Ser His Ser Ser Pro Glu Tyr Trp Ile Lys Ser
210                 215                 220 gga acc ctt gtc ccc gtc acc cga aac gat atc gtg aag ata gaa ggc      720
Gly Thr Leu Val Pro Val Thr Arg Asn Asp Ile Val Lys Ile Glu Gly
225                 230                 235                 240 atc gat gcc acc ggc ggc aat aac cag cct aac att ccg gat atc cct      768
Ile Asp Ala Thr Gly Gly Asn Asn Gln Pro Asn Ile Pro Asp Ile Pro
                245                 250                 255 gcg cac cta tgg tac ttc ggg tta att ggg aca tgt ctt                  807
Ala His Leu Trp Tyr Phe Gly Leu Ile Gly Thr Cys Leu
            260                 265

<210> SEQ ID NO 2
<211> LENGTH: 269
<212> TYPE: PRT
<213> ORGANISM: Thermomyces lanuginosus

<400> SEQUENCE: 2

Glu Val Ser Gln Asp Leu Phe Asn Gln Phe Asn Leu Phe Ala Gln Tyr
1               5                   10                  15

Ser Ala Ala Ala Tyr Cys Gly Lys Asn Asn Asp Ala Pro Ala Gly Thr
            20                  25                  30

Asn Ile Thr Cys Thr Gly Asn Ala Cys Pro Glu Val Glu Lys Ala Asp
        35                  40                  45

Ala Thr Phe Leu Tyr Ser Phe Glu Asp Ser Gly Val Gly Asp Val Thr
    50                  55                  60

Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Gly Asn Leu Asn Phe Asp
                85                  90                  95

Leu Lys Glu Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
        115                 120                 125

Glu Asp Ala Val Arg Glu His Pro Asp Tyr Arg Val Val Phe Thr Gly
    130                 135                 140

His Ser Leu Gly Gly Ala Leu Ala Thr Val Ala Gly Ala Asp Leu Arg
```

```
                145                 150                 155                 160
Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
        195                 200                 205

Arg Glu Phe Gly Tyr Ser His Ser Ser Pro Glu Tyr Trp Ile Lys Ser
    210                 215                 220

Gly Thr Leu Val Pro Val Thr Arg Asn Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gly Leu Ile Gly Thr Cys Leu
                260                 265

<210> SEQ ID NO 3
<211> LENGTH: 265
<212> TYPE: PRT
<213> ORGANISM: Absidia reflexa

<400> SEQUENCE: 3

Ser Ser Ser Ser Thr Gln Asp Tyr Arg Ile Ala Ser Glu Ala Glu Ile
1               5                   10                  15

Lys Ala His Thr Phe Tyr Thr Ala Leu Ser Ala Asn Ala Tyr Cys Arg
            20                  25                  30

Thr Val Ile Pro Gly Gly Arg Trp Ser Cys Pro His Cys Gly Val Ala
        35                  40                  45

Ser Asn Leu Gln Ile Thr Lys Thr Phe Ser Thr Leu Ile Thr Asp Thr
    50                  55                  60

Asn Val Leu Val Ala Val Gly Glu Lys Glu Lys Thr Ile Tyr Val Val
65                  70                  75                  80

Phe Arg Gly Thr Ser Ser Ile Arg Asn Ala Ile Ala Asp Ile Val Phe
                85                  90                  95

Val Pro Val Asn Tyr Pro Pro Val Asn Gly Ala Lys Val His Lys Gly
            100                 105                 110

Phe Leu Asp Ser Tyr Asn Glu Val Gln Asp Lys Leu Val Ala Glu Val
        115                 120                 125

Lys Ala Gln Leu Asp Arg His Pro Gly Tyr Lys Ile Val Val Thr Gly
    130                 135                 140

His Ser Leu Gly Gly Ala Thr Ala Val Leu Ser Ala Leu Asp Leu Tyr
145                 150                 155                 160

His His Gly His Ala Asn Ile Glu Ile Tyr Thr Gln Gly Gln Pro Arg
                165                 170                 175

Ile Gly Thr Pro Ala Phe Ala Asn Tyr Val Ile Gly Thr Lys Ile Pro
            180                 185                 190

Tyr Gln Arg Leu Val His Glu Arg Asp Ile Val Pro His Leu Pro Pro
        195                 200                 205

Gly Ala Phe Gly Phe Leu His Ala Gly Glu Glu Phe Trp Ile Met Lys
    210                 215                 220

Asp Ser Ser Leu Arg Val Cys Pro Asn Gly Ile Glu Thr Asp Asn Cys
225                 230                 235                 240

Ser Asn Ser Ile Val Pro Phe Thr Ser Val Ile Asp His Leu Ser Tyr
                245                 250                 255
```

```
Leu Asp Met Asn Thr Gly Leu Cys Leu
            260             265

<210> SEQ ID NO 4
<211> LENGTH: 264
<212> TYPE: PRT
<213> ORGANISM: Absidia corymbifera

<400> SEQUENCE: 4

Ser Ser Ser Thr Gln Asp Tyr Arg Ile Ala Ser Glu Ala Glu Ile Lys
1               5                   10                  15

Ala His Thr Phe Tyr Thr Ala Leu Ser Ala Asn Ala Tyr Cys Arg Thr
            20                  25                  30

Val Ile Pro Gly Gly Gln Trp Ser Cys Pro His Cys Asp Val Ala Pro
        35                  40                  45

Asn Leu Asn Ile Thr Lys Thr Phe Thr Thr Leu Ile Thr Asp Thr Asn
50                  55                  60

Val Leu Val Ala Val Gly Glu Asn Glu Lys Thr Ile Tyr Val Val Phe
65                  70                  75                  80

Arg Gly Thr Ser Ser Ile Arg Asn Ala Ile Ala Asp Ile Val Phe Val
                85                  90                  95

Pro Val Asn Tyr Pro Pro Val Asn Gly Ala Lys Val His Lys Gly Phe
            100                 105                 110

Leu Asp Ser Tyr Asn Glu Val Gln Asp Lys Leu Val Ala Glu Val Lys
        115                 120                 125

Ala Gln Leu Asp Arg His Pro Gly Tyr Lys Ile Val Val Thr Gly His
    130                 135                 140

Ser Leu Gly Gly Ala Thr Ala Val Leu Ser Ala Leu Asp Leu Tyr His
145                 150                 155                 160

His Gly His Asp Asn Ile Glu Ile Tyr Thr Gln Gly Gln Pro Arg Ile
                165                 170                 175

Gly Thr Pro Glu Phe Ala Asn Tyr Val Ile Gly Thr Lys Ile Pro Tyr
            180                 185                 190

Gln Arg Leu Val Asn Glu Arg Asp Ile Val Pro His Leu Pro Pro Gly
        195                 200                 205

Ala Phe Gly Phe Leu His Ala Gly Glu Glu Phe Trp Ile Met Lys Asp
    210                 215                 220

Ser Ser Leu Arg Val Cys Pro Asn Gly Ile Glu Thr Asp Asn Cys Ser
225                 230                 235                 240

Asn Ser Ile Val Pro Phe Thr Ser Val Ile Asp His Leu Ser Tyr Leu
                245                 250                 255

Asp Met Asn Thr Gly Leu Cys Leu
            260

<210> SEQ ID NO 5
<211> LENGTH: 269
<212> TYPE: PRT
<213> ORGANISM: Rhizomucor miehei

<400> SEQUENCE: 5

Ser Ile Asp Gly Gly Ile Arg Ala Ala Thr Ser Gln Glu Ile Asn Glu
1               5                   10                  15

Leu Thr Tyr Tyr Thr Thr Leu Ser Ala Asn Ser Tyr Cys Arg Thr Val
            20                  25                  30

Ile Pro Gly Ala Thr Trp Asp Cys Ile His Cys Asp Ala Thr Glu Asp
        35                  40                  45
```

-continued

```
Leu Lys Ile Ile Lys Thr Trp Ser Thr Leu Ile Tyr Asp Thr Asn Ala
 50                  55                  60

Met Val Ala Arg Gly Asp Ser Glu Lys Thr Ile Tyr Ile Val Phe Arg
 65                      70                  75                  80

Gly Ser Ser Ser Ile Arg Asn Trp Ile Ala Asp Leu Thr Phe Val Pro
                     85                  90                  95

Val Ser Tyr Pro Pro Val Ser Gly Thr Lys Val His Lys Gly Phe Leu
                100                 105                 110

Asp Ser Tyr Gly Glu Val Gln Asn Glu Leu Val Ala Thr Val Leu Asp
                115                 120                 125

Gln Phe Lys Gln Tyr Pro Ser Tyr Lys Val Ala Val Thr Gly His Ser
130                 135                 140

Leu Gly Gly Ala Thr Ala Leu Leu Cys Ala Leu Asp Leu Tyr Gln Arg
145                 150                 155                 160

Glu Glu Gly Leu Ser Ser Asn Leu Phe Leu Tyr Thr Gln Gly Gln
                165                 170                 175

Pro Arg Val Gly Asp Pro Ala Phe Ala Asn Tyr Val Val Ser Thr Gly
                180                 185                 190

Ile Pro Tyr Arg Arg Thr Val Asn Glu Arg Asp Ile Val Pro His Leu
                195                 200                 205

Pro Pro Ala Ala Phe Gly Phe Leu His Ala Gly Glu Glu Tyr Trp Ile
210                 215                 220

Thr Asp Asn Ser Pro Glu Thr Val Gln Val Cys Thr Ser Asp Leu Glu
225                 230                 235                 240

Thr Ser Asp Cys Ser Asn Ser Ile Val Pro Phe Thr Ser Val Leu Asp
                245                 250                 255

His Leu Ser Tyr Phe Gly Ile Asn Thr Gly Leu Cys Thr
                260                 265

<210> SEQ ID NO 6
<211> LENGTH: 271
<212> TYPE: PRT
<213> ORGANISM: Rhizopus oryzae

<400> SEQUENCE: 6

Ser Ala Ser Asp Gly Gly Lys Val Val Ala Thr Thr Ala Gln Ile
 1               5                  10                  15

Gln Glu Phe Thr Lys Tyr Ala Gly Ile Ala Ala Thr Ala Tyr Cys Arg
                 20                  25                  30

Ser Val Val Pro Gly Asn Lys Trp Asp Cys Val Gln Cys Gln Lys Trp
                 35                  40                  45

Val Pro Asp Gly Lys Ile Ile Thr Thr Phe Thr Ser Leu Leu Ser Asp
 50                  55                  60

Thr Asn Gly Tyr Val Leu Arg Ser Asp Lys Gln Lys Thr Ile Tyr Leu
 65                  70                  75                  80

Val Phe Arg Gly Thr Asn Ser Phe Arg Ser Ala Ile Thr Asp Ile Val
                 85                  90                  95

Phe Asn Phe Ser Asp Tyr Lys Pro Val Lys Gly Ala Lys Val His Ala
                100                 105                 110

Gly Phe Leu Ser Ser Tyr Glu Gln Val Val Asn Asp Tyr Phe Pro Val
                115                 120                 125

Val Gln Glu Gln Leu Thr Ala His Pro Thr Tyr Lys Val Ile Val Thr
130                 135                 140

Gly His Ser Leu Gly Gly Ala Gln Ala Leu Leu Ala Gly Met Asp Leu
145                 150                 155                 160
```

```
Tyr Gln Arg Glu Pro Arg Leu Ser Pro Lys Asn Leu Ser Ile Phe Thr
                165                 170                 175

Val Gly Gly Pro Arg Val Gly Asn Pro Thr Phe Ala Tyr Tyr Val Glu
            180                 185                 190

Ser Thr Gly Ile Pro Phe Gln Arg Thr Val His Lys Arg Asp Ile Val
        195                 200                 205

Pro His Val Pro Pro Gln Ser Phe Gly Phe Leu His Pro Gly Val Glu
    210                 215                 220

Ser Trp Ile Lys Ser Gly Thr Ser Asn Val Gln Ile Cys Thr Ser Glu
225                 230                 235                 240

Ile Glu Thr Lys Asp Cys Ser Asn Ser Ile Val Pro Phe Thr Ser Ile
                245                 250                 255

Leu Asp His Leu Ser Tyr Phe Asp Ile Asn Glu Gly Ser Cys Leu
                260                 265                 270

<210> SEQ ID NO 7
<211> LENGTH: 267
<212> TYPE: PRT
<213> ORGANISM: Aspergillus niger

<400> SEQUENCE: 7

Thr Ala Gly His Ala Leu Ala Ala Ser Thr Gln Gly Ile Ser Glu Asp
1               5                   10                  15

Leu Tyr Ser Arg Leu Val Glu Met Ala Thr Ile Ser Gln Ala Ala Tyr
                20                  25                  30

Ala Asp Leu Cys Asn Ile Pro Ser Thr Ile Ile Lys Gly Glu Lys Ile
            35                  40                  45

Tyr Asn Ser Gln Thr Asp Ile Asn Gly Trp Ile Leu Arg Asp Asp Ser
    50                  55                  60

Ser Lys Glu Ile Ile Thr Val Phe Arg Gly Thr Gly Ser Asp Thr Asn
65                  70                  75                  80

Leu Gln Leu Asp Thr Asn Tyr Thr Leu Thr Pro Phe Asp Thr Leu Pro
                85                  90                  95

Gln Cys Asn Gly Cys Glu Val His Gly Gly Tyr Tyr Ile Gly Trp Val
            100                 105                 110

Ser Val Gln Asp Gln Val Glu Ser Leu Val Lys Gln Gln Val Ser Gln
        115                 120                 125

Tyr Pro Asp Tyr Ala Leu Thr Val Thr Gly His Ser Leu Gly Ala Ser
    130                 135                 140

Leu Ala Ala Leu Thr Ala Ala Gln Leu Ser Ala Thr Tyr Asp Asn Ile
145                 150                 155                 160

Arg Leu Tyr Thr Phe Gly Glu Pro Arg Ser Gly Asn Gln Ala Phe Ala
                165                 170                 175

Ser Tyr Met Asn Asp Ala Phe Gln Ala Ser Ser Pro Asp Thr Thr Gln
            180                 185                 190

Tyr Phe Arg Val Thr His Ala Asn Asp Gly Ile Pro Asn Leu Pro Pro
        195                 200                 205

Val Glu Gln Gly Tyr Ala His Gly Gly Val Glu Tyr Trp Ser Val Asp
    210                 215                 220

Pro Tyr Ser Ala Gln Asn Thr Phe Val Cys Thr Gly Asp Glu Val Gln
225                 230                 235                 240

Cys Cys Glu Ala Gln Gly Gly Gln Gly Val Asn Asn Ala His Thr Thr
                245                 250                 255

Tyr Phe Gly Met Thr Ser Gly Ala Cys Thr Trp
```

```
                    260                 265

<210> SEQ ID NO 8
<211> LENGTH: 266
<212> TYPE: PRT
<213> ORGANISM: Aspergillus tubingensis

<400> SEQUENCE: 8

Thr Ala Gly His Ala Leu Ala Ala Ser Thr Gln Gly Ile Ser Glu Asp
1               5                   10                  15

Leu Tyr Ser Arg Leu Val Glu Met Ala Thr Ile Ser Gln Ala Ala Tyr
            20                  25                  30

Ala Asp Leu Cys Asn Ile Pro Ser Thr Ile Ile Lys Gly Glu Lys Ile
        35                  40                  45

Tyr Asn Ser Gln Thr Asp Ile Asn Gly Trp Ile Leu Arg Asp Asp Ser
    50                  55                  60

Ser Lys Glu Ile Ile Thr Val Phe Arg Gly Thr Gly Ser Asp Thr Asn
65                  70                  75                  80

Leu Gln Leu Asp Thr Asn Tyr Thr Leu Thr Pro Phe Asp Thr Leu Pro
                85                  90                  95

Gln Cys Asn Ser Cys Glu Val His Gly Gly Tyr Tyr Ile Gly Trp Ile
            100                 105                 110

Ser Val Gln Asp Gln Val Glu Ser Leu Val Gln Gln Val Ser Gln
        115                 120                 125

Phe Pro Asp Tyr Ala Leu Thr Val Thr Gly His Ser Leu Gly Ala Ser
    130                 135                 140

Leu Ala Ala Leu Thr Ala Ala Gln Leu Ser Ala Thr Tyr Asp Asn Ile
145                 150                 155                 160

Arg Leu Tyr Thr Phe Gly Glu Pro Arg Ser Asn Gln Ala Phe Ala Ser
                165                 170                 175

Tyr Met Asn Asp Ala Phe Gln Ala Ser Ser Pro Asp Thr Thr Gln Tyr
            180                 185                 190

Phe Arg Val Thr His Ala Asn Asp Gly Ile Pro Asn Leu Pro Pro Ala
        195                 200                 205

Asp Glu Gly Tyr Ala His Gly Val Val Glu Tyr Trp Ser Val Asp Pro
    210                 215                 220

Tyr Ser Ala Gln Asn Thr Phe Val Cys Thr Gly Asp Glu Val Gln Cys
225                 230                 235                 240

Cys Glu Ala Gln Gly Gly Gln Gly Val Asn Asn Ala His Thr Thr Tyr
                245                 250                 255

Phe Gly Met Thr Ser Gly His Cys Thr Trp
            260                 265

<210> SEQ ID NO 9
<211> LENGTH: 276
<212> TYPE: PRT
<213> ORGANISM: Fusarium oxysporum

<400> SEQUENCE: 9

Ala Val Gly Val Thr Thr Thr Asp Phe Ser Asn Phe Lys Phe Tyr Ile
1               5                   10                  15

Gln His Gly Ala Ala Ala Tyr Cys Asn Ser Glu Ala Ala Ala Gly Ser
            20                  25                  30

Lys Ile Thr Cys Ser Asn Asn Gly Cys Pro Thr Val Gln Gly Asn Gly
        35                  40                  45

Ala Thr Ile Val Thr Ser Phe Val Gly Ser Lys Thr Gly Ile Gly Gly
```

```
                50                  55                  60
Tyr Val Ala Thr Asp Ser Ala Arg Lys Glu Ile Val Val Ser Phe Arg
 65                  70                  75                  80

Gly Ser Ile Asn Ile Arg Asn Trp Leu Thr Asn Leu Asp Phe Gly Gln
                 85                  90                  95

Glu Asp Cys Ser Leu Val Ser Gly Cys Gly Val His Ser Gly Phe Gln
            100                 105                 110

Arg Ala Trp Asn Glu Ile Ser Ser Gln Ala Thr Ala Ala Val Ala Ser
        115                 120                 125

Ala Arg Lys Ala Asn Pro Ser Phe Asn Val Ile Ser Thr Gly His Ser
130                 135                 140

Leu Gly Gly Ala Val Ala Val Leu Ala Ala Ala Asn Leu Arg Val Gly
145                 150                 155                 160

Gly Thr Pro Val Asp Ile Tyr Thr Tyr Gly Ser Pro Arg Val Gly Asn
                165                 170                 175

Ala Gln Leu Ser Ala Phe Val Ser Asn Gln Ala Gly Gly Glu Tyr Arg
            180                 185                 190

Val Thr His Ala Asp Asp Pro Val Pro Arg Leu Pro Pro Leu Ile Phe
        195                 200                 205

Gly Tyr Arg His Thr Thr Pro Glu Phe Trp Leu Ser Gly Gly Gly Gly
210                 215                 220

Asp Lys Val Asp Tyr Thr Ile Ser Asp Val Lys Val Cys Glu Gly Ala
225                 230                 235                 240

Ala Asn Leu Gly Cys Asn Gly Gly Thr Leu Gly Leu Asp Ile Ala Ala
                245                 250                 255

His Leu His Tyr Phe Gln Ala Thr Asp Ala Cys Asn Ala Gly Gly Phe
            260                 265                 270

Ser Trp Arg Arg
        275

<210> SEQ ID NO 10
<211> LENGTH: 273
<212> TYPE: PRT
<213> ORGANISM: Fusarium heterosporum

<400> SEQUENCE: 10

Thr Val Thr Thr Gln Asp Leu Ser Asn Phe Arg Phe Tyr Leu Gln His
 1               5                  10                  15

Ala Asp Ala Ala Tyr Cys Asn Phe Asn Thr Ala Val Gly Lys Pro Val
             20                  25                  30

His Cys Ser Ala Gly Asn Cys Pro Asp Ile Glu Lys Asp Ala Ala Ile
         35                  40                  45

Val Val Gly Ser Val Val Gly Thr Lys Thr Gly Ile Gly Ala Tyr Val
     50                  55                  60

Ala Thr Asp Asn Ala Arg Lys Glu Ile Val Val Ser Val Arg Gly Ser
 65                  70                  75                  80

Ile Asn Val Arg Asn Trp Ile Thr Asn Phe Asn Phe Gly Gln Lys Thr
             85                  90                  95

Cys Asp Leu Val Ala Gly Cys Gly Val His Thr Gly Phe Leu Asp Ala
            100                 105                 110

Trp Glu Glu Val Ala Ala Asn Val Lys Ala Ala Val Ser Ala Ala Lys
        115                 120                 125

Thr Ala Asn Pro Thr Phe Lys Phe Val Val Thr Gly His Ser Leu Gly
130                 135                 140
```

```
Gly Ala Val Ala Thr Ile Ala Ala Ala Tyr Leu Arg Lys Asp Gly Phe
145                 150                 155                 160

Pro Phe Asp Leu Tyr Thr Tyr Gly Ser Pro Arg Val Gly Asn Asp Phe
                165                 170                 175

Phe Ala Asn Phe Val Thr Gln Gln Thr Gly Ala Glu Tyr Arg Val Thr
            180                 185                 190

His Gly Asp Asp Pro Val Pro Arg Leu Pro Ile Val Phe Gly Tyr
        195                 200                 205

Arg His Thr Ser Pro Glu Tyr Trp Leu Asn Gly Gly Pro Leu Asp Lys
    210                 215                 220

Asp Tyr Thr Val Thr Glu Ile Lys Val Cys Glu Gly Ile Ala Asn Val
225                 230                 235                 240

Met Cys Asn Gly Gly Thr Ile Gly Leu Asp Ile Leu Ala His Ile Thr
                245                 250                 255

Tyr Phe Gln Ser Met Ala Thr Cys Ala Pro Ile Ala Ile Pro Trp Lys
            260                 265                 270

Arg

<210> SEQ ID NO 11
<211> LENGTH: 278
<212> TYPE: PRT
<213> ORGANISM: Aspergillus oryzae

<400> SEQUENCE: 11

Asp Ile Pro Thr Thr Gln Leu Glu Asp Phe Lys Phe Trp Val Gln Tyr
1               5                   10                  15

Ala Ala Ala Thr Tyr Cys Pro Asn Asn Tyr Val Ala Lys Asp Gly Glu
                20                  25                  30

Lys Leu Asn Cys Ser Val Gly Asn Cys Pro Asp Val Glu Ala Ala Gly
            35                  40                  45

Ser Thr Val Lys Leu Ser Phe Ser Asp Asp Thr Ile Thr Asp Thr Ala
        50                  55                  60

Gly Phe Val Ala Val Asp Asn Thr Asn Lys Ala Ile Val Val Ala Phe
65                  70                  75                  80

Arg Gly Ser Tyr Ser Ile Arg Asn Trp Val Thr Asp Ala Thr Phe Pro
                85                  90                  95

Gln Thr Asp Pro Gly Leu Cys Asp Gly Cys Lys Ala Glu Leu Gly Phe
            100                 105                 110

Trp Thr Ala Trp Lys Val Val Arg Asp Arg Ile Ile Lys Thr Leu Asp
        115                 120                 125

Glu Leu Lys Pro Glu His Ser Asp Tyr Lys Ile Val Val Val Gly His
    130                 135                 140

Ser Leu Gly Ala Ala Ile Ala Ser Leu Ala Ala Ala Asp Leu Arg Thr
145                 150                 155                 160

Lys Asn Tyr Asp Ala Ile Leu Tyr Ala Tyr Ala Ala Pro Arg Val Ala
                165                 170                 175

Asn Lys Pro Leu Ala Glu Phe Ile Thr Asn Gln Gly Asn Asn Tyr Arg
            180                 185                 190

Phe Thr His Asn Asp Asp Pro Val Pro Lys Leu Pro Leu Leu Thr Met
        195                 200                 205

Gly Tyr Val His Ile Ser Pro Glu Tyr Tyr Ile Thr Ala Pro Asp Asn
    210                 215                 220

Thr Thr Val Thr Asp Asn Gln Val Thr Val Leu Asp Gly Tyr Val Asn
225                 230                 235                 240
```

```
Phe Lys Gly Asn Thr Gly Thr Ser Gly Gly Leu Pro Asp Leu Leu Ala
                    245                 250                 255

Phe His Ser His Val Trp Tyr Phe Ile His Ala Asp Ala Cys Lys Gly
                260                 265                 270

Pro Gly Leu Pro Leu Arg
            275

<210> SEQ ID NO 12
<211> LENGTH: 278
<212> TYPE: PRT
<213> ORGANISM: Penicillium camemberti

<400> SEQUENCE: 12

Asp Val Ser Thr Ser Glu Leu Asp Gln Phe Glu Phe Trp Val Gln Tyr
1               5                   10                  15

Ala Ala Ala Ser Tyr Tyr Glu Ala Asp Tyr Thr Ala Gln Val Gly Asp
                20                  25                  30

Lys Leu Ser Cys Ser Lys Gly Asn Cys Pro Glu Val Glu Ala Thr Gly
                35                  40                  45

Ala Thr Val Ser Tyr Asp Phe Ser Asp Ser Thr Ile Thr Asp Thr Ala
        50                  55                  60

Gly Tyr Ile Ala Val Asp His Thr Asn Ser Ala Val Val Leu Ala Phe
65                  70                  75                  80

Arg Gly Ser Tyr Ser Val Arg Asn Trp Val Ala Asp Ala Thr Phe Val
                85                  90                  95

His Thr Asn Pro Gly Leu Cys Asp Gly Cys Leu Ala Glu Leu Gly Phe
            100                 105                 110

Trp Ser Ser Trp Lys Leu Val Arg Asp Asp Ile Ile Lys Glu Leu Lys
        115                 120                 125

Glu Val Val Ala Gln Asn Pro Asn Tyr Glu Leu Val Val Val Gly His
130                 135                 140

Ser Leu Gly Ala Ala Val Ala Thr Leu Ala Ala Thr Asp Leu Arg Gly
145                 150                 155                 160

Lys Gly Tyr Pro Ser Ala Lys Leu Tyr Ala Tyr Ala Ser Pro Arg Val
                165                 170                 175

Gly Asn Ala Ala Leu Ala Lys Tyr Ile Thr Ala Gln Gly Asn Asn Phe
            180                 185                 190

Arg Phe Thr His Thr Asn Asp Pro Val Pro Lys Leu Pro Leu Leu Ser
        195                 200                 205

Met Gly Tyr Val His Val Ser Pro Glu Tyr Trp Ile Thr Ser Pro Asn
210                 215                 220

Asn Ala Thr Val Ser Thr Ser Asp Ile Lys Val Ile Asp Gly Asp Val
225                 230                 235                 240

Ser Phe Asp Gly Asn Thr Gly Thr Gly Leu Pro Leu Leu Thr Asp Phe
                245                 250                 255

Glu Ala His Ile Trp Tyr Phe Val Gln Val Asp Ala Gly Lys Gly Pro
            260                 265                 270

Gly Leu Pro Phe Lys Arg
        275

<210> SEQ ID NO 13
<211> LENGTH: 270
<212> TYPE: PRT
<213> ORGANISM: Aspergillus foetidus

<400> SEQUENCE: 13
```

```
Ser Val Ser Thr Ser Thr Leu Asp Glu Leu Gln Leu Phe Ala Gln Trp
  1               5                  10                  15

Ser Ala Ala Ala Tyr Cys Ser Asn Asn Ile Asp Ser Lys Asp Ser Asn
             20                  25                  30

Leu Thr Cys Thr Ala Asn Ala Cys Pro Ser Val Glu Glu Ala Ser Thr
         35                  40                  45

Thr Met Leu Leu Glu Phe Asp Leu Thr Asn Asp Phe Gly Gly Thr Ala
     50                  55                  60

Gly Phe Leu Ala Ala Asp Asn Thr Asn Lys Arg Leu Val Val Ala Phe
 65                  70                  75                  80

Arg Gly Ser Ser Thr Ile Glu Asn Trp Ile Ala Asn Leu Asp Phe Ile
                 85                  90                  95

Leu Glu Asp Asn Asp Asp Leu Cys Thr Gly Cys Lys Val His Thr Gly
             100                 105                 110

Phe Trp Lys Ala Trp Glu Ser Ala Ala Asp Glu Leu Thr Ser Lys Ile
         115                 120                 125

Lys Ser Ala Met Ser Thr Tyr Ser Gly Tyr Thr Leu Tyr Phe Thr Gly
     130                 135                 140

His Ser Leu Gly Gly Ala Leu Ala Thr Leu Gly Ala Thr Val Leu Arg
145                 150                 155                 160

Asn Asp Gly Tyr Ser Val Glu Leu Tyr Thr Tyr Gly Cys Pro Arg Ile
                 165                 170                 175

Gly Asn Tyr Ala Leu Ala Glu His Ile Thr Ser Gln Gly Ser Gly Ala
             180                 185                 190

Asn Phe Arg Val Thr His Leu Asn Asp Ile Val Pro Arg Val Pro Pro
         195                 200                 205

Met Asp Phe Gly Phe Ser Gln Pro Ser Pro Glu Tyr Trp Ile Thr Ser
     210                 215                 220

Gly Asn Gly Ala Ser Val Thr Ala Ser Asp Ile Glu Val Ile Glu Gly
225                 230                 235                 240

Ile Asn Ser Thr Ala Gly Asn Ala Gly Glu Ala Thr Val Ser Val Leu
                 245                 250                 255

Ala His Leu Trp Tyr Phe Phe Ala Ile Ser Glu Cys Leu Leu
             260                 265                 270

<210> SEQ ID NO 14
<211> LENGTH: 270
<212> TYPE: PRT
<213> ORGANISM: Aspergillus niger

<400> SEQUENCE: 14

Ser Val Ser Thr Ser Thr Leu Asp Glu Leu Gln Leu Phe Ser Gln Trp
  1               5                  10                  15

Ser Ala Ala Ala Tyr Cys Ser Asn Asn Ile Asp Ser Asp Asp Ser Asn
             20                  25                  30

Val Thr Cys Thr Ala Asp Ala Cys Pro Ser Val Glu Glu Ala Ser Thr
         35                  40                  45

Lys Met Leu Leu Glu Phe Asp Leu Thr Asn Asn Phe Gly Gly Thr Ala
     50                  55                  60

Gly Phe Leu Ala Ala Asp Asn Thr Asn Lys Arg Leu Val Val Ala Phe
 65                  70                  75                  80

Arg Gly Ser Ser Thr Ile Lys Asn Trp Ile Ala Asp Leu Asp Phe Ile
                 85                  90                  95

Leu Gln Asp Asn Asp Asp Leu Cys Thr Gly Cys Lys Val His Thr Gly
             100                 105                 110
```

```
Phe Trp Lys Ala Trp Glu Ala Ala Asp Asn Leu Thr Ser Lys Ile
            115                 120                 125
Lys Ser Ala Met Ser Thr Tyr Ser Gly Tyr Thr Leu Tyr Phe Thr Gly
130                 135                 140
His Ser Leu Gly Gly Ala Leu Ala Thr Leu Gly Ala Thr Val Leu Arg
145                 150                 155                 160
Asn Asp Gly Tyr Ser Val Glu Leu Tyr Thr Tyr Gly Cys Pro Arg Val
                165                 170                 175
Gly Asn Tyr Ala Leu Ala Glu His Ile Thr Ser Gln Gly Ser Gly Ala
            180                 185                 190
Asn Phe Pro Val Thr His Leu Asn Asp Ile Val Pro Arg Val Pro Pro
        195                 200                 205
Met Asp Phe Gly Phe Ser Gln Pro Ser Pro Glu Tyr Trp Ile Thr Ser
    210                 215                 220
Gly Thr Gly Ala Ser Val Thr Ala Ser Asp Ile Glu Leu Ile Glu Gly
225                 230                 235                 240
Ile Asn Ser Thr Ala Gly Asn Ala Gly Glu Ala Thr Val Asp Val Leu
                245                 250                 255
Ala His Leu Trp Tyr Phe Phe Ala Ile Ser Glu Cys Leu Leu
            260                 265                 270

<210> SEQ ID NO 15
<211> LENGTH: 269
<212> TYPE: PRT
<213> ORGANISM: Aspergillus oryzae

<400> SEQUENCE: 15

Asp Val Ser Ser Ser Leu Leu Asn Asn Leu Asp Leu Phe Ala Gln Tyr
1               5                   10                  15
Ser Ala Ala Ala Tyr Cys Asp Glu Asn Leu Asn Ser Thr Gly Thr Lys
            20                  25                  30
Leu Thr Cys Ser Val Gly Asn Cys Pro Leu Val Glu Ala Ala Ser Thr
        35                  40                  45
Gln Ser Leu Asp Glu Phe Asn Glu Ser Ser Tyr Gly Asn Pro Ala
    50                  55                  60
Gly Tyr Leu Ala Ala Asp Glu Thr Asn Lys Leu Leu Val Leu Ser Phe
65                  70                  75                  80
Arg Gly Ser Ala Asp Leu Ala Asn Trp Val Ala Asn Leu Asn Phe Gly
                85                  90                  95
Leu Glu Asp Ala Ser Asp Leu Cys Ser Gly Cys Glu Val His Ser Gly
            100                 105                 110
Phe Trp Lys Ala Trp Ser Glu Ile Ala Asp Thr Ile Thr Ser Lys Val
            115                 120                 125
Glu Ser Ala Leu Ser Asp His Ser Asp Tyr Ser Leu Val Leu Thr Gly
130                 135                 140
His Ser Tyr Gly Ala Ala Leu Ala Ala Leu Ala Thr Ala Leu Arg
145                 150                 155                 160
Asn Ser Gly His Ser Val Glu Leu Tyr Asn Tyr Gly Gln Pro Arg Leu
                165                 170                 175
Gly Asn Glu Ala Leu Ala Thr Tyr Ile Thr Asp Gln Asn Lys Gly Gly
            180                 185                 190
Asn Tyr Arg Val Thr His Thr Asn Asp Ile Val Pro Lys Leu Pro Pro
        195                 200                 205
Thr Leu Leu Gly Tyr His His Phe Ser Pro Glu Tyr Tyr Ile Ser Ser
```

-continued

```
                210                 215                 220
Ala Asp Glu Ala Thr Val Thr Thr Thr Asp Val Thr Glu Val Thr Gly
225                 230                 235                 240

Ile Asp Ala Thr Gly Gly Asn Asp Gly Thr Asp Gly Thr Ser Ile Asp
                245                 250                 255

Ala His Arg Trp Tyr Phe Ile Tyr Ile Ser Glu Cys Ser
                260                 265

<210> SEQ ID NO 16
<211> LENGTH: 251
<212> TYPE: PRT
<213> ORGANISM: Landerina penisapora

<400> SEQUENCE: 16

Pro Gln Asp Ala Tyr Thr Ala Ser His Ala Asp Leu Val Lys Tyr Ala
1               5                   10                  15

Thr Tyr Ala Gly Leu Ala Tyr Gln Thr Thr Asp Ala Trp Pro Ala Ser
                20                  25                  30

Arg Thr Val Pro Lys Asp Thr Thr Leu Ile Ser Ser Phe Asp His Thr
                35                  40                  45

Leu Lys Gly Ser Ser Gly Tyr Ile Ala Phe Asn Glu Pro Cys Lys Glu
    50                  55                  60

Ile Ile Val Ala Tyr Arg Gly Thr Asp Ser Leu Ile Asp Trp Leu Thr
65                  70                  75                  80

Asn Leu Asn Phe Asp Lys Thr Ala Trp Pro Ala Asn Ile Ser Asn Ser
                85                  90                  95

Leu Val His Glu Gly Phe Leu Asn Ala Tyr Leu Val Ser Met Gln Gln
                100                 105                 110

Val Gln Glu Ala Val Asp Ser Leu Leu Ala Lys Cys Pro Asp Ala Thr
                115                 120                 125

Ile Ser Phe Thr Gly His Ser Leu Gly Gly Ala Leu Ala Cys Ile Ser
    130                 135                 140

Met Val Asp Thr Ala Gln Arg His Arg Gly Ile Lys Met Gln Met Phe
145                 150                 155                 160

Thr Tyr Gly Gln Pro Arg Thr Gly Asn Gln Ala Phe Ala Glu Tyr Val
                165                 170                 175

Glu Asn Leu Gly His Pro Val Phe Arg Val Val Tyr Arg His Asp Ile
                180                 185                 190

Val Pro Arg Met Pro Pro Met Asp Leu Gly Phe Gln His His Gly Gln
                195                 200                 205

Glu Val Trp Tyr Glu Gly Asp Glu Asn Ile Lys Phe Cys Lys Gly Glu
    210                 215                 220

Gly Glu Asn Leu Thr Cys Glu Leu Gly Val Pro Phe Ser Glu Leu Asn
225                 230                 235                 240

Ala Lys Asp His Ser Glu Tyr Pro Gly Met His
                245                 250
```

DETERGENT COMPOSITIONS

CROSS-REFERENCES TO RELATED APPLICATIONS

This application claims priority under 35 U.S.C. §119(e) to U.S. Provisional Application Ser. No. 60/761,188 filed Jan. 23, 2006, U.S. Provisional Application Ser. No. 60/796,267 filed Apr. 28, 2006, and U.S. Provisional Application Ser. No. 60/854,787 filed Oct. 27, 2006.

FIELD OF THE INVENTION

This invention relates to compositions comprising lipases and fabric hueing agents and processes for making and using such products.

BACKGROUND OF THE INVENTION

The appearance of lipase enzymes suitable for detergent applications gave the formulator a new approach to improve grease removal. Such enzymes catalyse the hydrolysis of triglycerides which form a major component of many commonly encountered fatty soils such as sebum, animal fats (e.g. lard, ghee, butter) and vegetable oils (e.g. olive oil, sunflower oil, peanut oil). However these enzymes typically showed weak performance in the first wash cycle and typically came with a malodor arising, it is believed, from hydrolysis of fats present in dairy soils like milks, cream, butter and yogurt. While not being bound by theory, it is believed that such soils are prone to lipase-induced malodor generation as they contain triglycerides functionalized with short chain (e.g. $C_4$) fatty acyl units which release malodorous volatile fatty acids after lipolysis. Even the when the performance of such enzymes was improved, the malodor issue remained. Thus, the use of this technology was severely limited.

We have found that the combination of a fabric hueing agent with certain lipase variants gives rise to an improved cleaning performance benefit, while minimising unacceptable malodor. Without wishing to be bound by theory, it is believed that the following mechanisms are likely to give rise to such benefits: selected lipase variants increase the level of grease removal thus leading to better accessibility of the fabric hueing agent to the fabric surface and hence, improved deposition. The resulting combination of improved oily soil removal and shading colorant deposition leads to a improvement in fabric appearance; even where oily soil isn't adequately removed, the hydrolysis of fats into more hydrophilic fatty acids, mono- and di-glycerides leads to improved shading colorant deposition and, hence, cleaning perception; and the presence of dye molecules deposited in the oily soils present on fabrics may inhibit enzyme activity that gives rise to malodor.

SUMMARY OF THE INVENTION

The present invention relates to compositions comprising a fabric hueing agent and a lipase variant with reduced potential for odor generation and a good relative performance, without the attachment of a C-terminal extension. The lipase variant is obtained by introducing mutations in one or more regions identified in the parent lipase. The variant thus obtained must have a lipase activity which is not less than 80% of the parent lipase's activity expressed as Relative Performance.

BRIEF DESCRIPTION OF THE FIGURES

FIG. 1 shows the alignment of lipases.

SEQUENCE LISTINGS

SEQ ID NO: 1 shows the DNA sequence encoding lipase from *Thermomyces lanoginosus*.
SEQ ID NO: 2 shows the amino acid sequence of a lipase from *Thermomyces lanoginosus*.
SEQ ID NO: 3 shows the amino acid sequence of a lipase from *Absidia reflexa*.
SEQ ID NO: 4 shows the amino acid sequence of a lipase from *Absidia corymbifera*.
SEQ ID NO: 5 shows the amino acid sequence of a lipase from *Rhizomucor miehei*.
SEQ ID NO: 6 shows the amino acid sequence of a lipase from *Rhizopus oryzae*.
SEQ ID NO: 7 shows the amino acid sequence of a lipase from *Aspergillus niger*.
SEQ ID NO: 8 shows the amino acid sequence of a lipase from *Aspergillus tubingensis*.
SEQ ID NO: 9 shows the amino acid sequence of a lipase from *Fusarium oxysporrum*.
SEQ ID NO: 10 shows the amino acid sequence of a lipase from *Fusarium heterosporum*.
SEQ ID NO: 11 shows the amino acid sequence of a lipase from *Aspergillus oryzae*.
SEQ ID NO: 12 shows the amino acid sequence of a lipase from *Penicillium camemberti*.
SEQ ID NO: 13 shows the amino acid sequence of a lipase from *Aspergillus foetidus*.
SEQ ID NO: 14 shows the amino acid sequence of a lipase from *Aspergillus niger*.
SEQ ID NO: 15 shows the amino acid sequence of a lipase from *Aspergillus oryzae*.
SEQ ID NO: 16 shows the amino acid sequence of a lipase from *Landerina penisapora*.

DETAILED DESCRIPTION OF THE INVENTION

Definitions

As used herein, the term "cleaning composition" includes, unless otherwise indicated, granular or powder-form all-purpose or "heavy-duty" washing agents, especially laundry detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, laundry bars, mouthwashes, denture cleaners, car or carpet shampoos, bathroom cleaners; hair shampoos and hair-rinses; shower gels and foam baths and metal cleaners; as well as cleaning auxiliaries such as bleach additives and "stain-stick" or pre-treat types.

As used herein the term 'fabric hueing agent' means dyes or pigments which when formulated in detergent compositions can deposit onto a fabric when said fabric is contacted with a wash liquor comprising said detergent compositions thus altering the tint of said fabric. For the purposes of the present application, fluorescent optical brighteners are not considered fabric hueing agents.

As used herein, the phrase "is independently selected from the group consisting of . . ." means that moieties or elements that are selected from the referenced Markush group can be the same, can be different or any mixture of elements.

The test methods disclosed in the Test Methods Section of the present application must be used to determine the respective values of the parameters of Applicants' inventions.

Unless otherwise noted, all component or composition levels are in reference to the active level of that component or composition, and are exclusive of impurities, for example, residual solvents or by-products, which may be present in commercially available sources.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All documents cited are, in relevant part, incorporated herein by reference; the citation of any document is not to be construed as an admission that it is prior art with respect to the present invention.

Compositions

The compositions of the present invention may contain from about 0.00003% to about 0.1%, from about 0.00008% to about 0.05%, or even from about 0.0001% to about 0.04%, fabric hueing agent and from about 0.0005% to about 0.1%, from about 0.001% to about 0.05%, or even from about 0.002% to about 0.03% lipase.

Such compositions may take any form, for example, the form of a cleaning composition and/or a treatment composition.

The balance of any aspects of the aforementioned cleaning compositions is made up of one or more adjunct materials.

Suitable Lipase Variants

The lipase of the composition of the present invention is a lipase variant with no C-terminal extension but with mutations introduced in certain regions of a parent lipase whereby the tendency to odor generation is reduced.

Parent Lipase

The parent lipase may be a fungal lipase with an amino acid sequence having at least 50% homology as defined in the section "Homology and aligment" to the sequence of the *T. lanuginosus* lipase shown in SEQ ID NO: 2.

The parent lipase may be a yeast polypeptide such as a *Candida, Kluyveromyces, Pichia, Saccharomyces, Schizosaccharomyces*, or *Yarrowia* polypeptide; or more preferably a filamentous fungal polypeptide such as an *Acremonium, Aspergillus, Aureobasidium, Cryptococcus, Filobasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium*, or *Trichoderma* polypeptide.

In a preferred aspect, the parent lipase is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide having lipase activity.

In another preferred aspect, the parent lipase is an *Aspergillus aculeatus, Aspergillus awamori, Aspergillus fumigatus, Aspergillus foetidus, Aspergillus japonicus, Aspergillus nidulans, Aspergillus niger, Aspergillus oryzae, Aspergillus turbigensis, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Thermomyces lanoginosus* (synonym: *Humicola lanuginose*), *Mucor miehei, Myceliophthora thermophila, Neurospora crassa, Penicillium purpurogenum, Trichoderma harzianum, Trichoderma koningii, Trichoderma longibrachiatum, Trichoderma reesei*, or *Trichoderma viride* polypeptide.

In another preferred aspect, the parent lipase is a *Thermomyces* lipase.

In a more preferred aspect, the parent lipase is a *Thermomyces lanuginosus* lipase. In an even more preferred embodiment the parent lipase is the lipase of SEQ ID NO: 2.

Identification of Regions and Substitutions.

The positions referred to in Region I through Region IV below are the positions of the amino acid residues in SEQ ID NO:2. To find the corresponding (or homologous) positions in a different lipase, the procedure described in "Homology and alignment" is used.

Substitutions in Region I

Region I consists of amino acid residues surrounding the N-terminal residue E1. In this region it is preferred to substitute an amino acid of the parent lipase with a more positive amino acid. Amino acid residues corresponding to the following positions are comprised by Region I: 1 to 11 and 223-239. The following positions are of particular interest: 1, 2, 4, 8, 11, 223, 227, 229, 231, 233, 234 and 236. In particular the following substitutions have been identified: X1N/*, X4V, X227G, X231R and X233R.

In a preferred embodiment the parent lipase has at least 80%, such as 85% or 90%, such as at least 95% or 96% or 97% or 98% or 99%, identity to SEQ ID NO:2. In a most preferred embodiment the parent lipase is identical to SEQ ID NO: 2.

Substitutions in Region II

Region II consists of amino acid residues in contact with substrate on one side of the acyl chain and one side of the alcohol part. In this region it is preferred to substitute an amino acid of the parent lipase with a more positive amino acid or with a less hydrophobic amino acid. Amino acid residues corresponding to the following positions are comprised by Region II: 202 to 211 and 249 to 269. The following positions are of particular interest: 202, 210, 211, 253, 254, 255, 256, 259. In particular the following substitutions have been identified: X202G, X210K/W/A, X255Y/V/A, X256K/R and X259G/M/Q/V.

In a preferred embodiment the parent lipase has at least 80%, such as 85% or 90%, such as at least 95% or 96% or 97% or 98% or 99%, identity to SEQ ID NO:2. In a most preferred embodiment the parent lipase is identical to SEQ ID NO: 2.

Substitutions in Region III

Region III consists of amino acid residues that form a flexible structure and thus allowing the substrate to get into the active site. In this region it is preferred to substitute an amino acid of the parent lipase with a more positive amino acid or a less hydrophobic amino acid. Amino acid residues corresponding to the following positions are comprised by Region III: 82 to 102. The following positions are of particular interest: 83, 86, 87, 90, 91, 95, 96, 99. In particular the following substitutions have been identified: X83T, X86V and X90A/R.

In a preferred embodiment the parent lipase has at least 80%, such as 85% or 90%, such as at least 95% or 96% or 97% or 98% or 99%, identity to SEQ ID NO:2. In a most preferred embodiment the parent lipase is identical to SEQ ID NO: 2.

Substitutions in Region IV

Region IV consists of amino acid residues that bind electrostatically to a surface. In this region it is preferred to substitute an amino acid of the parent lipase with a more positive amino acid. Amino acid residues corresponding to the following positions are comprised by Region IV: 27 and 54 to 62. The following positions are of particular interest: 27, 56, 57, 58, 60. In particular the following substitutions have been identified: X27R, X58N/AG/T/P and X60V/S/G/N/R/K/A/L.

In a preferred embodiment the parent lipase has at least 80%, such as 85% or 90%, such as at least 95% or 96% or 97% or 98% or 99%, identity to SEQ ID NO:2. In a most preferred embodiment the parent lipase is identical to SEQ ID NO: 2.

Amino Acids at Other Positions

The parent lipase may optionally comprise substitutions of other amino acids, particularly less than 10 or less than 5 such substitutions. Examples are substitutions corresponding to one or more of the positions 24, 37, 38, 46, 74, 81, 83, 115, 127, 131, 137, 143, 147, 150, 199, 200, 203, 206, 211, 263, 264, 265, 267 and 269 of the parent lipase. In a particular embodiment there is a substitution in at least one of the positions corresponding to position 81, 143, 147, 150 and 249. In a preferred embodiment the at least one substitution is selected from the group consisting of X81Q/E, X143S/C/N/D/A, X147M/Y, X150G/K and X249R/I/L.

The variant may comprise substitutions outside the defined Regions I to IV, the number of substitutions outside of the defined Regions I to IV is preferably less than six, or less than five, or less than four, or less than three, or less than two, such as five, or four, or three, or two or one. Alternatively, the variant does not comprise any substitution outside of the defined Regions I to IV.

Further substitutions may, e.g., be made according to principles known in the art, e.g. substitutions described in WO 92/05249, WO 94/25577, WO 95/22615, WO 97/04079 and WO 97/07202.

Parent Lipase Variants

In one aspect, said variant, when compared to said parent, comprising a total of at least three substitutions, said substitutions being selected from one or more of the following groups of substitutions:

a) at least two, or at least three, or at least four, or at least five, or at least six, such as two, three, four, five or six, substitutions in Region I, b) at least one, at least two, or at least three, or at least four, or at least five, or at least six, such as one, two, three, four, five or six, substitution in Region II, c) at least one, at least two, or at least three, or at least four, or at least five, or at least six, such as one, two, three, four, five or six, substitution in Region III, d) and/or at least one, at least two, or at least three, or at least four, or at least five, or at least six, such as one, two, three, four, five or six, substitution in Region IV.

The variant may comprise substitutions, compared to the variant's parent, corresponding to those substitutions listed below in Table 1.

TABLE 1

Some particular variants.

| Region I | Region II | Region III | Region IV | Outside regions |
|---|---|---|---|---|
| X4V + X227G + X231R + X233R | X210K + X256K | X83T + X86V | X58A + X60S | X150G |
| X227G + X231R + X233R | X256K | X86V | X58N + X60S | X150G |
| X231R + X233R | X255Y | | | |
| X231R + X233R | X202G | | | |
| X227G + X231R + X233R | X256K | X86V | | |
| X4V + X231R + X233R | | | X58N + X60S | |
| X231R + X233R | | X90R | X58N + X60S | |
| X231R + X233R | X255V | X90A | | |
| X227G + X231R + X233R | X256K | X86V | X58N + X60S | X150G |
| X231R + X233R | X211L | | X58N + X60S | X147M |
| X231R + X233R | | | | X150K |

In a further particular embodiment the parent lipase is identical to SEQ ID NO:2, and the variants of Table 1 will thus be:

TABLE 2

Some particular variants of SEQ ID NO: 2

| Region I | Region II | Region III | Region IV | Outside regions |
|---|---|---|---|---|
| Q4V + L227G + T231R + N233R | E210K + P256K | S83T + I86V | S58A + V60S | A150G |
| L227G + T231R + N233R | P256K | I86V | S58N + V60S | A150G |

TABLE 2-continued

Some particular variants of SEQ ID NO: 2

| Region I | Region II | Region III | Region IV | Outside regions |
|---|---|---|---|---|
| T231R + N233R | I255Y | | | |
| T231R + N233R | I202G | | | |
| L227G + T231R + N233R | P256K | I86V | | |
| Q4V + T231R + N233R | | | S58N + V60S | |
| T231R + N233R | | I90R | S58N + V60S | |
| T231R + N233R | I255V | I90A | | |
| L227G + T231R + N233R | P256K | I86V | S58N + V60S | A150G |
| T231R + N233R | F211L | | S58N + V60S | L147M |
| X231R + X233R | | | | X150K |

Nomenclature for Amino Acid Modifications

In describing lipase variants according to the invention, the following nomenclature is used for ease of reference: Original amino acid(s):position(s):substituted amino acid(s)

According to this nomenclature, for instance the substitution of glutamic acid for glycine in position 195 is shown as G195E. A deletion of glycine in the same position is shown as G195*, and insertion of an additional amino acid residue such as lysine is shown as G195GK. Where a specific lipase contains a "deletion" in comparison with other lipases and an insertion is made in such a position this is indicated as *36D for insertion of an aspartic acid in position 36. Multiple mutations are separated by pluses, i.e.: R170Y+G195E, representing mutations in positions 170 and 195 substituting tyrosine and glutamic acid for arginine and glycine, respectively.

X231 indicates the amino acid in a parent polypeptide corresponding to position 231, when applying the described alignment procedure. X231R indicates that the amino acid is replaced with R. For SEQ ID NO:2 X is T, and X231R thus indicates a substitution of T in position 231 with R. Where the amino acid in a position (e.g. 231) may be substituted by another amino acid selected from a group of amino acids, e.g. the group consisting of R and P and Y, this will be indicated by X231R/P/Y.

In all cases, the accepted IUPAC single letter or triple letter amino acid abbreviation is employed.

Amino Acid Grouping

In this specification, amino acids are classified as negatively charged, positively charged or electrically neutral according to their electric charge at pH 10. Thus, negative amino acids are E, D, C (cysteine) and Y, particularly E and D. Positive amino acids are R, K and H, particularly R and K. Neutral amino acids are G, A, V, L, I, P, F, W, S, T, M, N, Q and C when forming part of a disulfide bridge. A substitution with another amino acid in the same group (negative, positive or neutral) is termed a conservative substitution.

The neutral amino acids may be divided into hydrophobic or non-polar (G, A, V, L, I, P, F, W and C as part of a disulfide bridge) and hydrophilic or polar (S, T, M, N, Q). In this specification, amino acids are classified as negatively charged, positively charged or electrically neutral according to their electric charge at pH 10. Thus, negative amino acids are E, D, C (cysteine) and Y, particularly E and D. Positive amino acids are R, K and H, particularly R and K. Neutral amino acids are G, A, V, L, I, P, F, W, S, T, M, N, Q and C when forming part of a disulfide bridge. A substitution with another amino acid in the same group (negative, positive or neutral) is termed a conservative substitution.

The neutral amino acids may be divided into hydrophobic or non-polar (G, A, V, L, I, P, F, W and C as part of a disulfide bridge) and hydrophilic or polar (S, T, M, N, Q).

Amino Acid Identity

The relatedness between two amino acid sequences or between two nucleotide sequences is described by the parameter "identity".

For purposes of the present invention, the alignment of two amino acid sequences is determined by using the Needle program from the EMBOSS package (http://emboss.org) version 2.8.0. The Needle program implements the global alignment algorithm described in Needleman, S. B. and Wunsch, C. D. (1970) J. Mol. Biol. 48, 443-453. The substitution matrix used is BLOSUM62, gap opening penalty is 10, and gap extension penalty is 0.5.

The degree of identity between an amino acid sequence of the present invention ("invention sequence"; e.g. amino acids 1 to 269 of SEQ ID NO:2) and a different amino acid sequence ("foreign sequence") is calculated as the number of exact matches in an alignment of the two sequences, divided by the length of the "invention sequence" or the length of the "foreign sequence", whichever is the shortest. The result is expressed in percent identity.

An exact match occurs when the "invention sequence" and the "foreign sequence" have identical amino acid residues in the same positions of the overlap. The length of a sequence is the number of amino acid residues in the sequence (e.g. the length of SEQ ID NO:2 is 269).

The parent lipase has an amino acid identity of at least 50% with the T. lanuginosus lipase (SEQ ID NO: 2), particularly at least 55%, at least 60%, at least 75%, at least 85%, at least 90%, more than 95% or more than 98%. In a particular embodiment the parent lipase is identical to the T. lanuginosus lipase (SEQ ID NO:2).

The above procedure may be used for calculation of identity as well as homology and for alignment. In the context of the present invention homology and alignment has been calculated as described below.

Homology and Alignment

For purposes of the present invention, the degree of homology may be suitably determined by means of computer programs known in the art, such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443-45), using GAP with the following settings for polypeptide sequence comparison: GAP creation penalty of 3.0 and GAP extension penalty of 0.1.

In the present invention, corresponding (or homologous) positions in the lipase sequences of *Absidia reflexa, Absidia corymbefera, Rhizmucor miehei, Rhizopus delemar, Aspergillus niger, Aspergillus tubigensis, Fusarium oxysporum, Fusarium heterosporum, Aspergillus oryzea,*

*Penicilium camembertii, Aspergillus foetidus, Aspergillus niger, Thermomyces lanoginosus* (synonym: *Humicola lanuginose*) and *Landerina penisapora* are defined by the alignment shown in FIG. 1.

To find the homologous positions in lipase sequences not shown in the alignment, the sequence of interest is aligned to the sequences shown in FIG. 1. The new sequence is aligned to the present alignment in FIG. 1 by using the GAP alignment to the most homologous sequence found by the GAP program. GAP is provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443-45). The following settings are used for polypeptide sequence comparison: GAP creation penalty of 3.0 and GAP extension penalty of 0.1.

The parent lipase has a homology of at least 50% with the *T. lanuginosus* lipase (SEQ ID NO: 2), particularly at least 55%, at least 60%, at least 75%, at least 85%, at least 90%, more than 95% or more than 98%. In a particular embodiment the parent lipase is identical to the *T. lanuginosus* lipase (SEQ ID NO:2).

Hybridization

The present invention also relates to isolated polypeptides having lipase activity which are encoded by polynucleotides which hybridize under very low stringency conditions, preferably low stringency conditions, more preferably medium stringency conditions, more preferably medium-high stringency conditions, even more preferably high stringency conditions, and most preferably very high stringency conditions with (i) nucleotides 178 to 660 of SEQ ID NO: 1, (ii) the cDNA sequence contained in nucleotides 178 to 660 of SEQ ID NO: 1, (iii) a subsequence of (i) or (ii), or (iv) a complementary strand of (i), (ii), or (iii) (J. Sambrook, E. F. Fritsch, and T. Maniatus, 1989, Molecular Cloning, A Laboratory Manual, 2d edition, Cold Spring Harbor, N.Y.). A subsequence of SEQ ID NO: 1 contains at least 100 contiguous nucleotides or preferably at least 200 contiguous nucleotides. Moreover, the subsequence may encode a polypeptide fragment which has lipase activity.

For long probes of at least 100 nucleotides in length, very low to very high stringency conditions are defined as prehybridization and hybridization at 42° C. in 5×SSPE, 0.3% SDS, 200 ug/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

DNA Sequence, Expression Vector, Host Cell, Production of Lipase

The invention provides a DNA sequence encoding the lipase of the invention, an expression vector harboring the DNA sequence, and a transformed host cell containing the DNA sequence or the expression vector. These may be obtained by methods known in the art.

The invention also provides a method of producing the lipase by culturing the transformed host cell under conditions conducive for the production of the lipase and recovering the lipase from the resulting broth. The method may be practiced according to principles known in the art.

Lipase Activity

-Lipase Activity on Tributyrin at Neutral pH (LU)

A substrate for lipase is prepared by emulsifying tributyrin (glycerin tributyrate) using gum Arabic as emulsifier. The hydrolysis of tributyrin at 30° C. at pH 7 or 9 is followed in a pH-stat titration experiment. One unit of lipase activity (1 LU) equals the amount of enzyme capable of releasing 1 micro mol butyric acid/min at pH 7.

-Benefit Risk

The Benefit Risk factor describing the performance compared to the reduced risk for odour smell is defined as: $BR=RP_{avg}/R$. Lipase variants described herein may have BRs greater than 1, greater than 1.1, or even greater than 1 to about 1000.

-Average Relative Performance

The procedure for calculating average relative performance (RPavg) is found in Example 5 of the present specification. Lipase variants described herein may have (RPavg) of at least 0.8, at least 1.1, at least 1.5, or even at least 2 to about 1000.

Suitable Fabric Hueing Agents

Fluorescent optical brighteners emit at least some visible light. In contrast, fabric hueing agents can alter the tint of a surface as they absorb at least a portion of the visible light spectrum. Suitable fabric hueing agents include dyes, dye-clay conjugates, and pigments that satisfy the requirements of Test Method 1 in the Test Method Section of the present specification. Suitable dyes include small molecule dyes and polymeric dyes. Suitable small molecule dyes include small molecule dyes selected from the group consisting of:

(1) Tris-Azo Direct Blue Dyes of the Formula

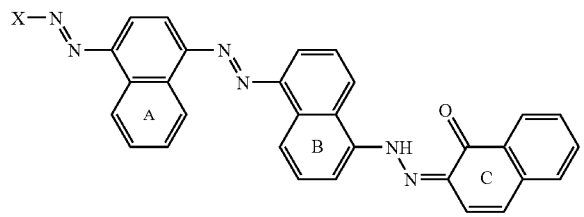

where at least two of the A, B and C napthyl rings are substituted by a sulfonate group, the C ring may be substituted at the 5 position by an $NH_2$ or NHPh group, X is a benzyl or naphthyl ring substituted with up to 2 sulfonate groups and may be substituted at the 2 position with an OH group and may also be substituted with an $NH_2$ or NHPh group.

(2) Bis-Azo Direct Violet Dyes of the Formula:

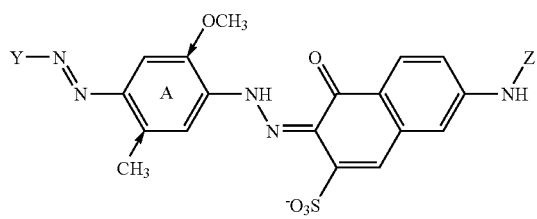

where Z is H or phenyl, the A ring is preferably substituted by a methyl and methoxy group at the positions indicated by arrows, the A ring may also be a naphthyl ring, the Y group is a benzyl or naphthyl ring, which is substituted by sulfate group and may be mono or disubstituted by methyl groups.

(3) Blue or Red Acid Dyes of the Formula

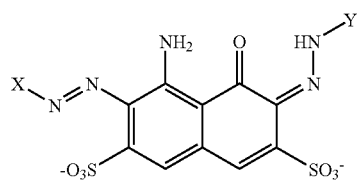

where at least one of X and Y must be an aromatic group. In one aspect, both the aromatic groups may be a substituted benzyl or naphthyl group, which may be substituted with non water-solubilising groups such as alkyl or alkyloxy or aryloxy groups, X and Y may not be substituted with water solubilising groups such as sulfonates or carboxylates. In another aspect, X is a nitro substituted benzyl group and Y is a benzyl group (4) Red Acid Dyes of the Structure

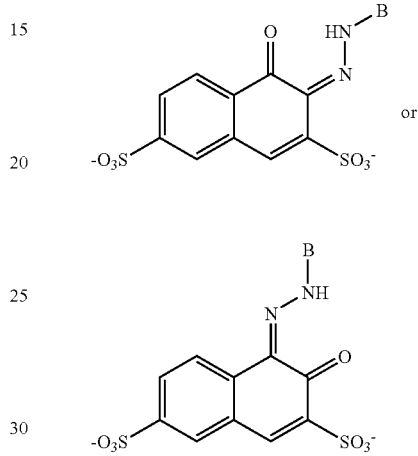

where B is a naphthyl or benzyl group that may be substituted with non water solubilising groups such as alkyl or alkyloxy or aryloxy groups, B may not be substituted with water solubilising groups such as sulfonates or carboxylates.

(5) Dis-Azo Dyes of the Structure

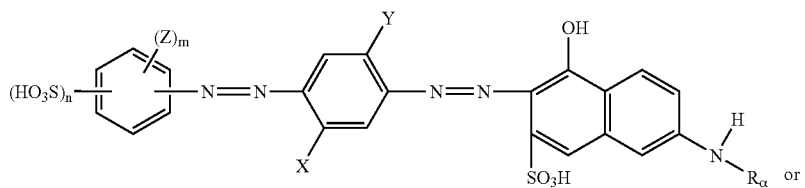

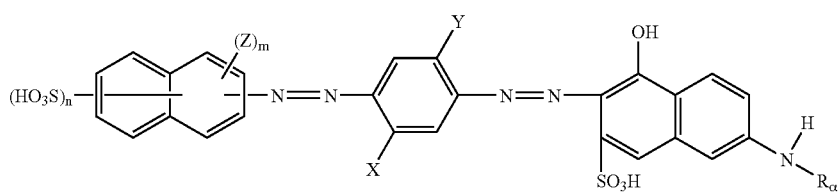

wherein X and Y, independently of one another, are each hydrogen, $C_1$-$C_4$ alkyl or $C_1$-$C_4$-alkoxy, Rα is hydrogen or aryl, Z is $C_1$-$C_4$ alkyl; $C_1$-$C_4$-alkoxy; halogen; hydroxyl or carboxyl, n is 1 or 2 and m is 0, 1 or 2, as well as corresponding salts thereof and mixtures thereof (6) Triphenylmethane Dyes of the Following Structures

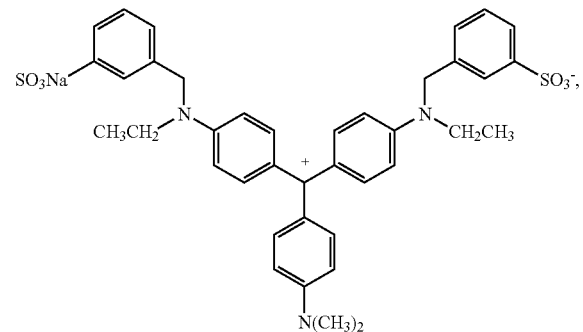

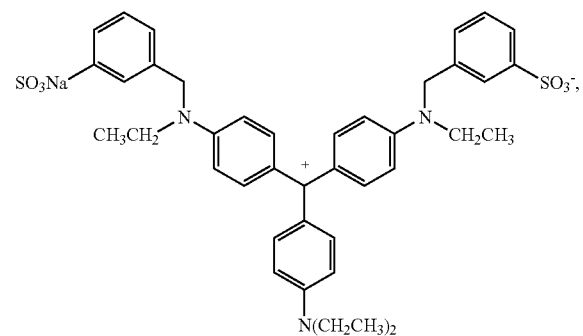

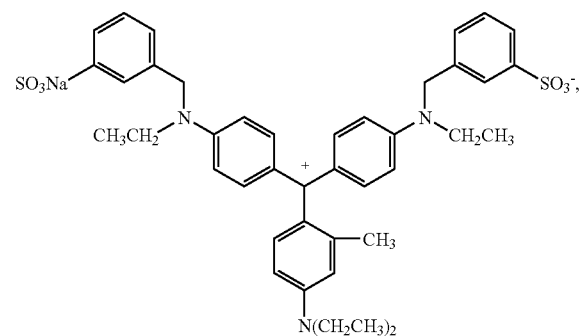

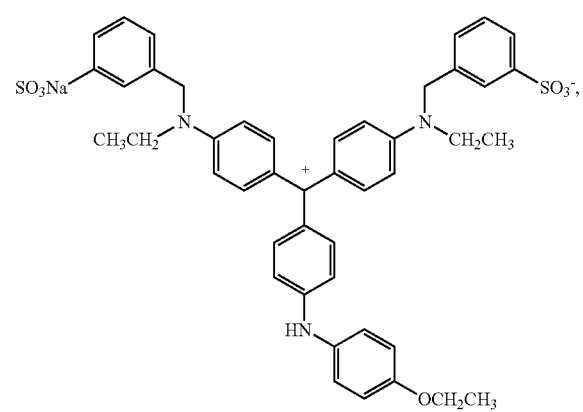

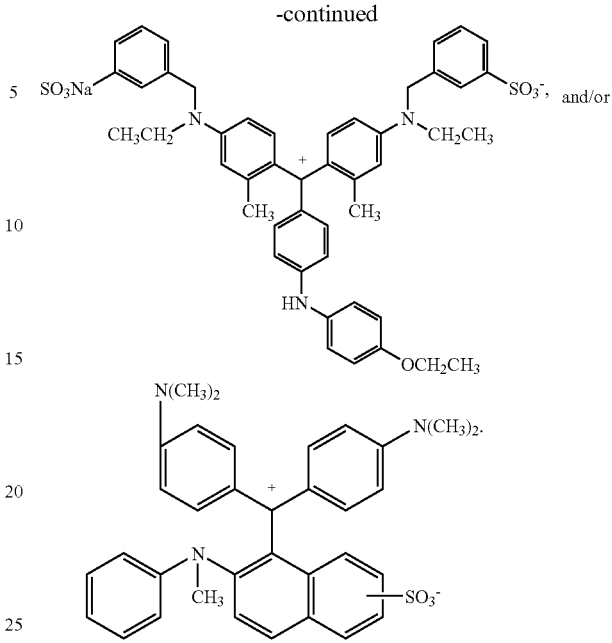

and mixtures thereof. In another aspect, suitable small molecule dyes include small molecule dyes selected from the group consisting of Colour Index (Society of Dyers and Colourists, Bradford, UK) numbers Direct Violet 9, Direct Violet 35, Direct Violet 48, Direct Violet 51, Direct Violet 66, Direct Blue 1, Direct Blue 71, Direct Blue 80, Direct Blue 279, Acid Red 17, Acid Red 88, Acid Red 150, Acid Violet 15, Acid Violet 17, Acid Violet 24, Acid Violet 49, Acid Blue 15, Acid Blue 17, Acid Blue 29, Acid Blue 40, Acid Blue 75, Acid Blue 80, Acid Blue 83, Acid Blue 90 and Acid Blue 113, Basic Violet 1, Basic Violet 3, Basic Violet 4, Basic Violet 10, Basic Violet 35, Basic Blue 3, Basic Blue 16, Basic Blue 22, Basic Blue 47, Basic Blue 66, Basic Blue 75, Basic Blue 159 and mixtures thereof.

Suitable polymeric dyes include polymeric dyes selected from the group consisting of polymers containing conjugated chromogens (dye-polymer conjugates) and polymers with chromogens co-polymerized into the backbone of the polymer and mixtures thereof.

In another aspect, suitable polymeric dyes include polymeric dyes selected from the group consisting of fabric-substantive colorants sold under the name of Liquitint® (Milliken, Spartanburg, S.C., USA), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. In still another aspect, suitable polymeric dyes include polymeric dyes selected from the group consisting of Liquitint® (Milliken, Spartanburg, S.C., USA) Violet CT, carboxymethyl cellulose (CMC) conjugated with a reactive blue, reactive violet or reactive red dye such as CMC conjugated with C.I. Reactive Blue 19, sold by Megazyme, Wicklow, Ireland under the product name AZO-CM-CELLULOSE, product code S-ACMC and mixtures thereof.

Suitable dye clay conjugates include dye clay conjugates selected from the group comprising at least one cationic/basic dye and a smectite clay, and mixtures thereof. In another aspect, suitable dye clay conjugates include dye clay conjugates selected from the group consisting of one cationic/basic dye selected from the group consisting of C.I. Basic Yellow 1 through 108, C.I. Basic Orange 1 through 69, C.I. Basic Red 1 through 118, C.I. Basic Violet 1 through 51, C.I. Basic Blue 1 through 164, C.I. Basic Green 1 through 14, C.I. Basic Brown 1 through 23, CI Basic Black 1 through 11, and a clay selected from the group consisting of Montmorillonite clay, Hectorite clay, Saponite clay and mixtures thereof. In still another aspect, suitable dye clay conjugates include dye clay conjugates selected from the group consisting of Montmorillonite Basic Blue B7 C.I. 42595 conjugate, Montmorillonite Basic Blue B9 C.I. 52015 conjugate, Montmorillonite Basic Violet V3 C.I. 42555 conjugate, Montmorillonite Basic Green GI C.I. 42040 conjugate, Montmorillonite Basic Red R1 C.I. 45160 conjugate, Montmorillonite C.I. Basic Black 2 conjugate, Hectorite Basic Blue B7 C.I. 42595 conjugate, Hectorite Basic Blue B9 C.I. 52015 conjugate, Hectorite Basic Violet V3 C.I. 42555 conjugate, Hectorite Basic Green GI C.I. 42040 conjugate, Hectorite Basic Red R1 C.I. 45160 conjugate, Hectorite C.I. Basic Black 2 conjugate, Saponite Basic Blue B7 C.I. 42595 conjugate, Saponite Basic Blue B9 C.I. 52015 conjugate, Saponite Basic Violet V3 C.I. 42555 conjugate, Saponite Basic Green GI C.I. 42040 conjugate, Saponite Basic Red R1 C.I. 45160 conjugate, Saponite C.I. Basic Black 2 conjugate and mixtures thereof.

Suitable pigments include pigments selected from the group consisting of flavanthrone, indanthrone, chlorinated indanthrone containing from 1 to 4 chlorine atoms, pyranthrone, dichloropyranthrone, monobromodichloropyranthrone, dibromodichloropyranthrone, tetrabromopyranthrone, perylene-3,4,9,10-tetracarboxylic acid diimide, wherein the imide groups may be unsubstituted or substituted by C1-C3-alkyl or a phenyl or heterocyclic radical, and wherein the phenyl and heterocyclic radicals may additionally carry substituents which do not confer solubility in water, anthrapyrimidinecarboxylic acid amides, violanthrone, isoviolanthrone, dioxazine pigments, copper phthalocyanine which may contain up to 2 chlorine atoms per molecule, polychloro-copper phthalocyanine or polybromochloro-copper phthalocyanine containing up to 14 bromine atoms per molecule and mixtures thereof. In another aspect, suitable pigments include pigments selected from the group consisting of Ultramarine Blue (C.I. Pigment Blue 29), Ultramarine Violet (C.I. Pigment Violet 15) and mixtures thereof.

The aforementioned fabric hueing agents can be used in combination (any mixture of fabric hueing agents can be used). Suitable fabric hueing agents can be purchased from Aldrich, Milwaukee, Wis., USA; Ciba Specialty Chemicals, Basel, Switzerland; BASF, Ludwigshafen, Germany; Dayglo Color Corporation, Mumbai, India; Organic Dyestuffs Corp., East Providence, R.I., USA; Dystar, Frankfurt, Germany; Lanxess, Leverkusen, Germany; Megazyme, Wicklow, Ireland; Clariant, Muttenz, Switzerland; Avecia, Manchester, UK and/or made in accordance with the examples contained herein.

Adjunct Materials

While not essential for the purposes of the present invention, the non-limiting list of adjuncts illustrated hereinafter are suitable for use in the instant compositions and may be desirably incorporated in certain embodiments of the invention, for example to assist or enhance cleaning performance, for treatment of the substrate to be cleaned, or to modify the aesthetics of the cleaning composition as is the case with perfumes, colorants, dyes or the like. The precise nature of these additional components, and levels of incorporation thereof, will depend on the physical form of the composition and the nature of the cleaning operation for which it is to be used. Suitable adjunct materials include, but are not limited to, surfactants, builders, chelating agents, dye transfer inhibiting agents, dispersants, additional enzymes, and enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids, solvents and/or pigments. In addition to the disclosure below, suitable examples of such other adjuncts and levels of use are found in U.S. Pat. Nos. 5,576,282, 6,306,812 B1 and 6,326,348 B1 that are incorporated by reference.

As stated, the adjunct ingredients are not essential to Applicants' compositions. Thus, certain embodiments of Applicants' compositions do not contain one or more of the following adjuncts materials: surfactants, builders, chelating agents, dye transfer inhibiting agents, dispersants, additional enzymes, and enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids, solvents and/or pigments. However, when one or more adjuncts are present, such one or more adjuncts may be present as detailed below:

Bleaching Agents—The cleaning compositions of the present invention may comprise one or more bleaching agents. Suitable bleaching agents other than bleaching catalysts include photobleaches, bleach activators, hydrogen peroxide, sources of hydrogen peroxide, pre-formed peracids and mixtures thereof. In general, when a bleaching agent is used, the compositions of the present invention may comprise from about 0.1% to about 50% or even from about 0.1% to about 25% bleaching agent by weight of the subject cleaning composition. Examples of suitable bleaching agents include:

(1) photobleaches for example sulfonated zinc phthalocyanine;

(2) preformed peracids: Suitable preformed peracids include, but are not limited to, compounds selected from the group consisting of percarboxylic acids and salts, percarbonic acids and salts, perimidic acids and salts, peroxymonosulfuric acids and salts, for example, Oxzone®, and mixtures thereof. Suitable percarboxylic acids include hydrophobic and hydrophilic peracids having the formula R—(C=O)O—O-M wherein R is an alkyl group, optionally branched, having, when the peracid is hydrophobic, from 6 to 14 carbon atoms, or from 8 to 12 carbon atoms and, when the peracid is hydrophilic, less than 6 carbon atoms or even less than 4 carbon atoms; and M is a counterion, for example, sodium, potassium or hydrogen;

(3) sources of hydrogen peroxide, for example, inorganic perhydrate salts, including alkali metal salts such as sodium salts of perborate (usually mono- or tetra-hydrate), percarbonate, persulphate, perphosphate, persilicate salts and mixtures thereof. In one aspect of the invention the inorganic perhydrate salts are selected from the group consisting of sodium salts of perborate, percarbonate and mixtures thereof. When employed, inorganic perhydrate salts are typically present in amounts of from 0.05 to 40 wt %, or 1 to 30 wt % of the overall composition and are typically incorporated into such compositions as a crystalline solid that may be coated. Suitable coatings include, inorganic salts such as alkali metal silicate, carbonate or borate salts or mixtures thereof, or organic materials such as water-soluble or dispersible polymers, waxes, oils or fatty soaps; and (4) bleach activators having R—(C=O)-L wherein R is an alkyl group, optionally branched, having, when the bleach activator is hydrophobic, from 6 to 14 carbon atoms, or from 8 to 12 carbon atoms and, when the bleach activator is hydrophilic, less than 6 carbon atoms or even less than 4 carbon atoms; and L is leaving group. Examples of suitable leaving groups are benzoic acid and derivatives thereof—especially benzene sulphonate. Suitable bleach activators include dodecanoyl oxybenzene sulphonate, decanoyl oxybenzene sulphonate, decanoyl oxybenzoic acid or salts thereof, 3,5,5-trimethyl hexanoyloxybenzene sulphonate, tetraacetyl ethylene diamine (TAED) and nonanoyloxybenzene sulphonate (NOBS). Suitable bleach activators are also disclosed in WO 98/17767. While any suitable bleach activator may be employed, in one aspect of the invention the subject cleaning composition may comprise NOBS, TAED or mixtures thereof.

When present, the peracid and/or bleach activator is generally present in the composition in an amount of from about 0.1 to about 60 wt %, from about 0.5 to about 40 wt % or even from about 0.6 to about 10 wt % based on the composition. One or more hydrophobic peracids or precursors thereof may be used in combination with one or more hydrophilic peracid or precursor thereof. The amounts of hydrogen peroxide source and peracid or bleach activator may be selected such that the molar ratio of available oxygen (from the peroxide source) to peracid is from 1:1 to 35:1, or even 2:1 to 10:1.

Surfactants—The cleaning compositions according to the present invention may comprise a surfactant or surfactant system wherein the surfactant can be selected from nonionic surfactants, anionic surfactants, cationic surfactants, ampholytic surfactants, zwitterionic surfactants, semi-polar nonionic surfactants and mixtures thereof. When present, surfactant is typically present at a level of from about 0.1% to about 60%, from about 1% to about 50% or even from about 5% to about 40% by weight of the subject composition.

Builders—The cleaning compositions of the present invention may comprise one or more detergent builders or builder systems. When a builder is used, the subject composition will typically comprise at least about 1%, from about 5% to about 60% or even from about 10% to about 40% builder by weight of the subject composition. Builders include, but are not limited to, the alkali metal, ammonium and alkanolammonium salts of polyphosphates, alkali metal silicates, alkaline earth and alkali metal carbonates, aluminosilicate builders and polycarboxylate compounds, ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof.

Chelating Agents—The cleaning compositions herein may contain a chelating agent. Suitable chelating agents include copper, iron and/or manganese chelating agents and mixtures thereof. When a chelating agent is used, the subject composition may comprise from about 0.005% to about 15% or even from about 3.0% to about 10% chelating agent by weight of the subject composition.

Dye Transfer Inhibiting Agents—The cleaning compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Brighteners—The cleaning compositions of the present invention can also contain additional components that may tint articles being cleaned, such as fluorescent brighteners. Suitable fluorescent brightener levels include lower levels of from about 0.01, from about 0.05, from about 0.1 or even from about 0.2 wt % to upper levels of 0.5 or even 0.75 wt %.

Dispersants—The compositions of the present invention can also contain dispersants. Suitable water-soluble organic materials include the homo- or co-polymeric acids or their salts, in which the polycarboxylic acid comprises at least two carboxyl radicals separated from each other by not more than two carbon atoms.

Additional Enzymes—The cleaning compositions can comprise one or more enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, mannanases, pectate lyases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is an enzyme cocktail that may comprise, for example, a protease and lipase in conjunction with amylase. When present in a cleaning composition, the aforementioned additional enzymes may be present at levels from about 0.00001% to about 2%, from about 0.0001% to about 1% or even from about 0.001% to about 0.5% enzyme protein by weight of the composition.

Enzyme Stabilizers—Enzymes for use in detergents can be stabilized by various techniques. The enzymes employed herein can be stabilized by the presence of water-soluble sources of calcium and/or magnesium ions in the finished compositions that provide such ions to the enzymes. In case of aqueous compositions comprising protease, a reversible protease inhibitor, such as a boron compound, can be added to further improve stability.

Catalytic Metal Complexes—Applicants' cleaning compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra(methylenephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. No. 5,597,936; U.S. Pat.

No. 5,595,967. Such cobalt catalysts are readily prepared by known procedures, such as taught for example in U.S. Pat. No. 5,597,936, and U.S. Pat. No. 5,595,967.

Compositions herein may also suitably include a transition metal complex of ligands such as bispidones (WO 05/042532 A1) and/or macropolycyclic rigid ligands—abbreviated as "MRLs". As a practical matter, and not by way of limitation, the compositions and processes herein can be adjusted to provide on the order of at least one part per hundred million of the active MRL species in the aqueous washing medium, and will typically provide from about 0.005 ppm to about 25 ppm, from about 0.05 ppm to about 10 ppm, or even from about 0.1 ppm to about 5 ppm, of the MRL in the wash liquor.

Suitable transition-metals in the instant transition-metal bleach catalyst include, for example, manganese, iron and chromium. Suitable MRLs include 5,12-diethyl-1,5,8,12-tetraazabicyclo[6.6.2]hexadecane.

Suitable transition metal MRLs are readily prepared by known procedures, such as taught for example in WO 00/32601, and U.S. Pat. No. 6,225,464.

Solvents—Suitable solvents include water and other solvents such as lipophilic fluids.

Examples of suitable lipophilic fluids include siloxanes, other silicones, hydrocarbons, glycol ethers, glycerine derivatives such as glycerine ethers, perfluorinated amines, perfluorinated and hydrofluoroether solvents, low-volatility nonfluorinated organic solvents, diol solvents, other environmentally-friendly solvents and mixtures thereof.

Processes of Making Compositions

The compositions of the present invention can be formulated into any suitable form and prepared by any process chosen by the formulator, non-limiting examples of which are described in Applicants' examples and in U.S. Pat. No. 4,990,280; U.S. 20030087791A1; U.S. 20030087790A1; U.S. 20050003983A1; U.S. 20040048764A1; U.S. Pat. Nos. 4,762,636; 6,291,412; U.S. 20050227891A1; EP 1070115A2; U.S. Pat. Nos. 5,879,584; 5,691,297; 5,574,005; 5,569,645; 5,565,422; 5,516,448; 5,489,392; 5,486,303 all of which are incorporated herein by reference.

Method of Use

The present invention includes a method for cleaning and/or treating a situs inter alia a surface or fabric. Such method includes the steps of contacting an embodiment of Applicants' cleaning composition, in neat form or diluted in a wash liquor, with at least a portion of a surface or fabric then optionally rinsing such surface or fabric. The surface or fabric may be subjected to a washing step prior to the aforementioned rinsing step. For purposes of the present invention, washing includes but is not limited to, scrubbing, and mechanical agitation. As will be appreciated by one skilled in the art, the cleaning compositions of the present invention are ideally suited for use in laundry applications. Accordingly, the present invention includes a method for laundering a fabric. The method comprises the steps of contacting a fabric to be laundered with a said cleaning laundry solution comprising at least one embodiment of Applicants' cleaning composition, cleaning additive or mixture thereof. The fabric may comprise most any fabric capable of being laundered in normal consumer use conditions. The solution preferably has a pH of from about 8 to about 10.5. The compositions may be employed at concentrations of from about 500 ppm to about 15,000 ppm in solution. The water temperatures typically range from about 5° C. to about 90° C. The water to fabric ratio is typically from about 1:1 to about 30:1.

Test Method 1

A protocol to define whether a dye or pigment material is a fabric hueing agent for the purpose of the invention is given here:

1.) Fill two tergotometer pots with 800 ml of Newcastle upon Tyne, UK, City Water (~12 grains per US gallon total hardness, supplied by Northumbrian Water, Pity Me, Durham, Co. Durham, UK).
2) Insert pots into tergotometer, with water temperature controlled at 30° C. and agitation set at 40 rpm for the duration of the experiment
3) Add 4.8 g of IEC-B detergent (IEC 60456 Washing Machine Reference Base Detergent Type B), supplied by wfk, Brüggen-Bracht, Germany, to each pot.
4) After two minutes, add 2.0 mg active colorant to the first pot.
5) After one minute, add 50 g of flat cotton vest (supplied by Warwick Equest, Consett, County Durham, UK), cut into 5 cm×5 cm swatches, to each pot.
6) After 10 minutes, drain the pots and re-fill with cold Newcastle upon Tyne City Water (16° C.)
7) After 2 minutes rinsing, remove fabrics
8) Repeat steps 3-7 for a further three cycles using the same treatments
9) Collect and line dry the fabrics indoors for 12 hours
10) Analyse the swatches using a Hunter Miniscan spectrometer fitted with D65 illuminant and UVA cutting filter, to obtain Hunter a (red-green axis) and Hunter b (yellow-blue axis) values.
11) Average the Hunter a and Hunter b values for each set of fabrics. If the fabrics treated with colorant under assessment show an average difference in hue of greater than 0.2 units on either the a axis or b axis, it is deemed to be a fabric hueing agent for the purpose of the invention.

EXAMPLES

Lipase Variants Examples

Chemicals used as buffers and substrates are commercial products of at least reagent grade.
Media and Solutions: LAS (Surfac PS™) and Zeolite A (Wessalith P™). Other ingredients used are standard laboratory reagents.
Materials: EMPA221 from EMPA St. Gallen, Lerchfeldstrasse 5, CH-9014 St. Gallen, Switzerland Example 1

Production of Enzyme

A plasmid containing the gene encoding the lipase is constructed and transformed into a suitable host cell using standard methods of the art.

Fermentation is carried out as a fed-batch fermentation using a constant medium temperature of 34° C. and a start volume of 1.2 liter. The initial pH of the medium is set to 6.5. Once the pH has increased to 7.0 this value is maintained through addition of 10% H3PO4. The level of dissolved oxygen in the medium is controlled by varying the agitation rate and using a fixed aeration rate of 1.0 liter air per liter medium per minute. The feed addition rate is maintained at a constant level during the entire fed-batch phase.

The batch medium contained maltose syrup as carbon source, urea and yeast extract as nitrogen source and a mixture of trace metals and salts. The feed added continuously during the fed-batch phase contains maltose syrup as carbon source whereas yeast extract and urea is added in order to assure a sufficient supply of nitrogen.

Purification of the lipase may be done by use of standard methods known in the art, e.g. by filtering the fermentation supernatant and subsequent hydrophobic chromatography and anion exchange, e.g. as described in EP 0 851 913, Example 3.

Example 2

AMSA—Automated Mechanical Stress Assay—for Calculation of Relative Performance (RP)

The enzyme variants of the present application are tested using the Automatic Mechanical Stress Assay (AMSA). With the AMSA test the wash performance of a large quantity of small volume enzyme-detergent solutions can be examined. The AMSA plate has a number of slots for test solutions and a lid firmly squeezing the textile swatch to be washed against all the slot openings. During the washing time, the plate, test solutions, textile and lid are vigorously shaken to bring the test solution in contact with the textile and apply mechanical stress. For further description see WO 02/42740 especially the paragraph "Special method embodiments" at page 23-24. The containers, which contain the detergent test solution, consist of cylindrical holes (6 mm diameter, 10 mm depth) in a metal plate. The stained fabric (test material) lies on the top of the metal plate and is used as a lid and seal on the containers. Another metal plate lies on the top of the stained fabric to avoid any spillage from each container. The two metal plates together with the stained fabric are vibrated up and down at a frequency of 30 Hz with an amplitude of 2 mm.

The assay is conducted under the experimental conditions specified below:

TABLE 3

| Test solution | 0.5 g/l LAS |
| --- | --- |
| | 0.52 g/l Na2CO3 |
| | 1.07 g/l Zeolite A |
| | 0.52 g/l Tri sodium Citrate |
| Test solution volume | 160 micro 1 |
| pH | As is (≈9.9) |
| Wash time | 20 minutes |
| Temperature | 30° C. |
| Water hardness | 15°dH |
| | Ratio of $Ca^{2+}/Mg^{2+}/NaHCO_3$: 4:1:7.5 |
| Enzyme concentration in test solution | 0.125, 0.25, 0.50, 1.0 mg enzyme protein/liter (mg ep/l) |
| Drying | Performance: After washing the textile pieces is immediately flushed in tap water and air-dried at 85 C in 5 min |
| | Odor: After washing the textile pieces is immediately flushed in tap water and dried at room temperature (20° C.) for 2 hours |
| Test material | Cream turmeric swatch as described below (EMPA221 used as cotton textile) |

Cream-turmeric swatches are prepared by mixing 5 g of turmeric (Santa Maria, Denmark) with 100 g cream (38% fat, Arla, Denmark) at 50° C., the mixture is left at this temperature for about 20 minutes and filtered (50° C.) to remove any undissolved particles. The mixture is cooled to 20° C.) woven cotton swatches, EMPA221, are immersed in the cream-turmeric mixture and afterwards allowed to dry at room temperature over night and frozen until use. The preparation of cream-turmeric swatches is disclosed in the patent application PA 2005 00775, filed 27 May 2005.

The performance of the enzyme variant is measured as the brightness of the colour of the textile samples washed with that specific enzyme variant. Brightness can also be expressed as the intensity of the light reflected from the textile sample when luminated with white light. When the textile is stained the intensity of the reflected light is lower, than that of a clean textile. Therefore the intensity of the reflected light can be used to measure wash performance of an enzyme variant.

Color measurements are made with a professional flatbed scanner (PFU DL2400pro), which is used to capture an image of the washed textile samples. The scans are made with a resolution of 200 dpi and with an output color depth of 24 bits. In order to get accurate results, the scanner is frequently calibrated with a Kodak reflective IT8 target.

To extract a value for the light intensity from the scanned images, a special designed software application is used (Novozymes Color Vector Analyzer). The program retrieves the 24 bit pixel values from the image and converts them into values for red, green and blue (RGB). The intensity value (Int) is calculated by adding the RGB values together as vectors and then taking the length of the resulting vector:

$$Int = \sqrt{r^2 + g^2 + b^2}.$$

The wash performance (P) of the variants is calculated in accordance with the formula:

$$P = Int(v) - Int(r) \text{ where}$$

Int(v) is the light intensity value of textile surface washed with the tested enzyme and Int(r) is the light intensity value of textile surface washed without the tested enzyme.

A relative performance score is given as the result of the AMSA wash in accordance with the definition: Relative Performance scores (RP) are summing up the performances (P) of the tested enzyme variants against the reference enzyme: RP=P (test enzyme)/P (reference enzyme). RPavg indicates the average relative performance compared to the reference enzyme at all four enzyme concentrations (0.125, 0.25, 0.5, 1.0 mg ep/l)

$$RPavg = avg(RP(0.125), RP(0.25)\ RP(0.5), RP(1.0))$$

A variant is considered to exhibit improved wash performance, if it performs better than the reference. In the context of the present invention the reference enzyme is the lipase of SEQ ID NO:2 with the substitutions T231R+N233R.

Example 3

GC—Gas Chromatograph—for Calculation of Risk Factor

The butyric acid release from the lipase washed swatches are measured by Solid Phase Micro Extraction Gas Chromatography (SPME-GC) using the following method. Four textile pieces (5 mm in diameter), washed in the specified solution in Table 3 containing 1 mg/l lipase, are transferred to a Gas Chromatograph (GC) vial. The samples are analysed on a Varian 3800 GC equipped with a Stabilwax-DA w/Integra-Guard column (30 m, 0.32 mm ID and 0.25 micro-m df) and a Carboxen PDMS SPME fibre (75 micro-m). Each sample is preincubated for 10 min at 40° C. followed by 20 min sampling with the SPME fibre in the head-space over the textile pieces. The sample is subsequently injected onto the column (injector temperature=250° C.). Column flow=2 ml Helium/min. Column oven temperature gradient: 0 min=40° C., 2 min=40° C., 22 min=240° C., 32 min=240° C. The butyric acid is detected by FID detection and the amount of butyric acid is calculated based on a butyric acid standard curve.

The Risk Performance Odour, R, of a lipase variant is the ratio between the amount of released butyric acid from the lipase variant washed swatch and the amount of released butyric acid from a swatch washed with the lipase of SEQ ID NO: 2 with the substitutions T231R+N233R (reference enzyme), after both values have been corrected for the amount of released butyric acid from a non-lipase washed swatch. The risk (R) of the variants is calculated in accordance with the below formula:

Odour=measured in micro g butyric acid developed at 1 mg enzyme protein/1 corrected for blank $\alpha_{test\ enzyme} = Odour_{test\ enzyme} - Blank$ $\alpha_{reference\ enzyme} = Odour_{reference\ enzyme} - Blank$ $R = \alpha_{test\ enzyme} / \alpha_{reference\ enzyme}$ A variant is considered to exhibit reduced odor compared to the reference, if the R factor is lower than 1.

Example 4

Activity (LU) Relative to Absorbance at 280 nm

The activity of a lipase relative to the absorbance at 280 nm is determined by the following assay LU/A280:

The activity of the lipase is determined as described above in the section Lipase activity. The absorbance of the lipase at 280 nm is measured (A280) and the ratio LU/A280 is calculated. The relative LU/A280 is calculated as the LU/A280 of the variant divided by the LU/A280 of a reference enzyme. In the context of the present invention the reference enzyme is the lipase of SEQ ID NO:2 with the substitutions T231R+N233R.

Example 5

BR—Benefit Risk

The Benefit Risk factor describing the performance compared to the reduced risk for odour smell is thus defined as:

$BR = RP_{avg}/R$

A variant is considered to exhibit improved wash performance and reduced odor, if the BR factor is higher than 1.

Applying the above methods the following results are obtained:

TABLE 4

| Variant | Mutations in SEQ ID NO: 2 | Average RP ($RP_{avg}$) | BR | LU/A280 |
|---|---|---|---|---|
| 1 | I202G + T231R + N233R | 0.84 | 1.41 | not determined |
| 2 | I86V + L227G + T231R + N233R + P256K | 1.08 | 1.52 | 1700 |
| 3 | Q4V + S58N + V60S + T231R + N233R | 0.87 | 1.73 | 1950 |
| 4 | S58N + V60S + I90R + T231R + N233R | 1.06 | 1.27 | 2250 |
| 5 | I255Y + T231R + N233R | 1.19 | 1.17 | 3600 |
| 6 | I90A + T231R + N233R + I255V | 1.13 | 1.14 | 2700 |
| Reference | T231R + N233R | 1.00 | 1.00 | 3650 |
| 7 | G91A + E99K + T231R + N233R + Q249R + 270H + 271T + 272P + 273S + 274S + 275G + 276R + 277G + 278G + 279H + 280R | 0.43 | not determined | 850 |
| 8 | G91A + E99K + T231R, N233R + Q249R + 270H + 271T + 272P + 273S + 274S + 275G + 276R + 277G + 278G | 0.13 | not determined | 500 |

The reference lipase and variants 7 and 8 in Table 4 are described in WO 2000/060063.

Example 6

BR—Benefit Risk

The Benefit Risk was measured for the variants listed in Table 5. The Benefit Risk factor was measured in the same way as described in Example 5 and it was found to be above 1 for all the listed variants.

TABLE 5

| Variant | Mutations in SEQ ID NO: 2 |
|---|---|
| Reference | T231R + N233R |
| 9 | L97V + T231R + N233R |
| 10 | A150G + T231R + N233R |
| 11 | I90R + T231R + N233R |

TABLE 5-continued

| Variant | Mutations in SEQ ID NO: 2 |
|---|---|
| 12 | I202V + T231R + N233R |
| 13 | L227G + T231R + N233R + P256K |
| 14 | I90A + T231R + N233R |
| 15 | T231R + N233R + I255P |
| 16 | I90V + I255V + T231R + N233R |
| 17 | F211L + L227G + T231R + N233R + I255L + P256K |
| 18 | S58N + V60S + T231R + N233R + Q249L |
| 19 | S58N + V60S + T231R + N233R + Q249I |
| 20 | A150G + L227G + T231R + N233R + P256K |
| 21 | K46L + S58N + V60S + T231R + N233R + Q249L + D254I |
| 22 | Q4L + E43T + K46I + S58N + V60S + T231R + N233R + Q249L + D254I |
| 23 | Q4L + S58N + V60S + T231R + N233R + Q249L + D254I |
| 24 | K46I + S58N + V60S + T231R + N233R + Q249L + D254L |
| 25 | K46L + S58N + V60S + K223I + T231R + N233R + D254I |
| 26 | E43T + K46I + S58N + V60S + T231R + N233R + Q249L + D254I |
| 27 | S58N + V60S + I86V + A150G + L227G + T231R + N233R + P256K |
| 28 | K24R + K46R + K74R + I86V + K98R + K127R + D137K + A150G + K223R + T231R + N233R |
| 29 | S58A + V60A + I86V + T231R + N233R |
| 30 | K24R + K46R + S58N + V60S + K74R + I86V + K98R + K127R + D137K + K223R + T231R + N233R |
| 31 | S58A + V60A + I86V + A150G + T231R + N233R |
| 32 | S58N + V60V + D62G + T231R + N233R |
| 33 | Q4V + S58N + V60S + I86V + T231R + N233R + Q249L |
| 34 | Q4V + S58N + V60S + I86V + A150G + T231R + N233R + I255V |
| 35 | Q4V + S58N + V60S + I90A + A150G + T231R + N233R + I255V |
| 36 | Y53A + S58N + V60S + T231R + N233R + P256L |
| 37 | I202L + T231R + N233R + I255A |
| 38 | S58A + V60S + I86V + A150G + L227G + T231R + N233R + P256K |
| 39 | D27R + S58N + V60S + I86V + A150G + L227G + T231R + N233R + P256K |
| 40 | V60K + I86V + A150G + L227G + T231R + N233R + P256K |
| 41 | Q4V + S58A + V60S + S83T + I86V + A150G + E210K + L227G + T231R + N233R + P256K |
| 42 | Q4V + V60K + S83T + I86V + A150G + L227G + T231R + N233R + P256K |
| 43 | D27R + V60K + I86V + A150G + L227G + T231R + N233R + P256K |
| 44 | Q4N + L6S + S58N + V60S + I86V + A150G + L227G + T231R + N233R + P256K |
| 45 | E1N + V60K + I86V + A150G + L227G + T231R + N233R + P256K |
| 46 | V60K + I86V + A150G + K223N + G225S + T231R + N233R + P256K |
| 47 | E210V + T231R + N233R + Q249R |
| 48 | S58N + V60S + E210V + T231R + N233R + Q249R |
| 49 | Q4V + V60K + I90R + T231R + N233R + I255V |
| 50 | Q4V + V60K + A150G + T231R + N233R |
| 51 | V60K + S83T + T231R + N233R |
| 52 | V60K + A150G + T231R + N233R + I255V |
| 53 | T231R + N233G + D234G |
| 54 | S58N + V60S + I86V + A150G + E210K + L227G + T231R + N233R + Q249R + P256K |
| 55 | S58N + V60S + I86V + A150G + E210K + L227G + T231R + N233R + I255A + P256K |
| 56 | S58N + V60S + I86V + A150G + G156R + E210K + L227G + T231R + N233R + I255A + P256K |
| 57 | S58T + V60K + I86V + N94K + A150G + E210V + L227G + T231R + N233R + P256K |
| 58 | S58T + V60K + I86V + D102A + A150G + L227G + T231R + N233R + P256K |
| 59 | S58T + V60K + I86V + D102A + A150G + E210V + L227G + T231R + N233R + P256K |
| 60 | S58T + V60K + S83T + I86V + N94K + A150G + E210V + L227G + T231R + N233R + P256K |
| 61 | S58A + V60S + I86V + T143S + A150G + L227G + T231R + N233R + P256K |
| 62 | G91S + D96V + D254R |
| 63 | V60L + G91M + T231W + Q249L |
| 64 | T37A + D96A + T231R + N233R + Q249G |
| 65 | E56G + E87D + T231R + N233R + D254A |
| 66 | E210K + T231R + N233R |
| 67 | D27H + E87Q + D96N + T231R + N233R + D254V |
| 68 | F181L + E210V + T231R + N233R |
| 69 | D27N + D96G + T231R + N233R |
| 70 | D96N + T231R + N233R |
| 71 | T231R + N233I + D234G |
| 72 | S58K + V60L + E210V + Q249R |
| 73 | S58H + V60L + E210V + Q249R |
| 74 | Q4V + F55V + I86V + T231R + N233R + I255V |
| 75 | Q4V + S58T + V60K + T199L + N200A + E210K + T231R + N233R + I255A + P256K |
| 76 | Q4V + D27N + V60K + T231R + N233R |
| 77 | I90F + I202P + T231R + N233R + I255L |
| 78 | S58N + V60S + D158N + T231R + N233R |
| 79 | S58N + V60S + S115K + T231R + N233R |
| 80 | S58N + V60S + L147M + A150G + F211L + T231R + N233R |
| 81 | V60K + A150G + T231R + N233R |
| 82 | I90V + L227G + T231R + N233R + P256K |
| 83 | T231R + N233R + I255S |
| 84 | I86G + T231R + N233R |
| 85 | V60K + I202V + E210K + T231R + N233R + I255A + P256K |
| 86 | I90G + I202L + T231R + N233R + I255S |
| 87 | S58G + V60G + T231R + N233R |

The reference lipase is described in WO 2000/060063.

Composition Examples

Unless otherwise indicated, materials can be obtained from Aldrich, P.O. Box 2060, Milwaukee, Wis. 53201, USA.

Examples 1-6

Granular laundry detergent compositions designed for hand-washing or top-loading washing machines.

|  | 1 (wt %) | 2 (wt %) | 3 (wt %) | 4 (wt %) | 5 (wt %) | 6 (wt %) |
|---|---|---|---|---|---|---|
| Linear alkylbenzenesulfonate | 20 | 22 | 20 | 15 | 20 | 20 |
| $C_{12-14}$ Dimethylhydroxyethyl ammonium chloride | 0.7 | 1 | 1 | 0.6 | 0.0 | 0.7 |
| AE3S | 0.9 | 0.0 | 0.9 | 0.0 | 0.0 | 0.9 |
| AE7 | 0.0 | 0.5 | 0.0 | 1 | 3 | 1 |
| Sodium tripolyphosphate | 23 | 30 | 23 | 17 | 12 | 23 |
| Zeolite A | 0.0 | 0.0 | 0.0 | 0.0 | 10 | 0.0 |
| 1.6R Silicate ($SiO_2$:$Na_2O$ ratio 1.6:1) | 7 | 7 | 7 | 7 | 7 | 7 |
| Sodium Carbonate | 15 | 14 | 15 | 18 | 15 | 15 |
| Polyacrylate MW 4500 | 1 | 0.0 | 1 | 1 | 1.5 | 1 |
| Carboxy Methyl Cellulose | 1 | 1 | 1 | 1 | 1 | 1 |
| Savinase ® 32.89 mg/g | 0.1 | 0.07 | 0.1 | 0.1 | 0.1 | 0.1 |
| Natalase ® 8.65 mg/g | 0.1 | 0.1 | 0.1 | 0.0 | 0.1 | 0.1 |
| Lipase† 18 mg/g | 0.03 | 0.07 | 0.3 | 0.1 | 0.07 | 0.4 |
| Fluorescent Brightener 1 | 0.06 | 0.0 | 0.06 | 0.18 | 0.06 | 0.06 |
| Fluorescent Brightener 2 | 0.1 | 0.06 | 0.1 | 0.0 | 0.1 | 0.1 |
| Diethylenetriamine pentaacetic acid | 0.6 | 0.3 | 0.6 | 0.25 | 0.6 | 0.6 |
| $MgSO_4$ | 1 | 1 | 1 | 0.5 | 1 | 1 |
| Sodium Percarbonate | 0.0 | 5.2 | 0.1 | 0.0 | 0.0 | 0.0 |
| Sodium Perborate Monohydrate | 4.4 | 0.0 | 3.85 | 2.09 | 0.78 | 3.63 |
| NOBS | 1.9 | 0.0 | 1.66 | — | 0.33 | 0.75 |
| TAED | 0.58 | 1.2 | 0.51 | — | 0.015 | 0.28 |
| Sulphonated zinc phthalocyanine | 0.0030 | — | 0.0012 | 0.0030 | 0.0021 | — |
| S-ACMC | 0.1 | 0.06 | — | — | — | — |
| Direct Violet 9 | — | — | 0.0003 | 0.0005 | 0.0003 | — |
| Ultramarine Blue | — | — | — | — | — | 0.2 |
| Sulfate/Moisture | Balance to 100% | Balance to 100% | Balance to 100% | Balance to 100% | Balance to 100% | Balance to 100% |

Any of the above compositions is used to launder fabrics at a concentration of 600-10000 ppm in water, with typical median conditions of 2500 ppm, 25° C., and a 25:1 water:cloth ratio.

Examples 7-10

Granular laundry detergent compositions designed for front-loading automatic washing machines.

|  | 7 (wt %) | 8 (wt %) | 9 (wt %) | 10 (wt %) |
|---|---|---|---|---|
| Linear alkylbenzenesulfonate | 8 | 7.1 | 7 | 6.5 |
| AE3S | 0 | 4.8 | 0 | 5.2 |
| Alkylsulfate | 1 | 0 | 1 | 0 |
| AE7 | 2.2 | 0 | 3.2 | 0 |
| $C_{10-12}$ Dimethyl hydroxyethylammonium chloride | 0.75 | 0.94 | 0.98 | 0.98 |
| Crystalline layered silicate ($\delta$-$Na_2Si_2O_5$) | 4.1 | 0 | 4.8 | 0 |
| Zeolite A | 20 | 0 | 17 | 0 |
| Citric Acid | 3 | 5 | 3 | 4 |
| Sodium Carbonate | 15 | 20 | 14 | 20 |
| Silicate 2R ($SiO_2$:$Na_2O$ at ratio 2:1) | 0.08 | 0 | 0.11 | 0 |
| Soil release agent | 0.75 | 0.72 | 0.71 | 0.72 |
| Acrylic Acid/Maleic Acid Copolymer | 1.1 | 3.7 | 1.0 | 3.7 |
| Carboxymethylcellulose | 0.15 | 1.4 | 0.2 | 1.4 |
| Protease (56.00 mg active/g) | 0.37 | 0.4 | 0.4 | 0.4 |
| Termamyl ® (21.55 mg active/g) | 0.3 | 0.3 | 0.3 | 0.3 |
| Lipase† (18.00 mg active/g) | 0.05 | 0.15 | 0.1 | 0.5 |
| Natalase ® (8.65 mg active/g) | 0.1 | 0.14 | 0.14 | 0.3 |
| TAED | 3.6 | 4.0 | 3.6 | 4.0 |
| Percarbonate | 13 | 13.2 | 13 | 13.2 |
| Na salt of Ethylenediamine-N,N'-disuccinic acid, (S,S) isomer (EDDS) | 0.2 | 0.2 | 0.2 | 0.2 |
| Hydroxyethane di phosphonate (HEDP) | 0.2 | 0.2 | 0.2 | 0.2 |

-continued

|  | 7 (wt %) | 8 (wt %) | 9 (wt %) | 10 (wt %) |
|---|---|---|---|---|
| $MgSO_4$ | 0.42 | 0.42 | 0.42 | 0.42 |
| Perfume | 0.5 | 0.6 | 0.5 | 0.6 |
| Suds suppressor agglomerate | 0.05 | 0.1 | 0.05 | 0.1 |
| Soap | 0.45 | 0.45 | 0.45 | 0.45 |
| Sodium sulfate | 22 | 33 | 24 | 30 |
| Sulphonated zinc phthalocyanine (active) | 0.0007 | 0.0012 | 0.0007 | — |
| S-ACMC | 0.01 | 0.01 | — | 0.01 |
| Direct Violet 9 (active) | — | — | 0.0001 | 0.0001 |
| Water & Miscellaneous | Balance to 100% | Balance to 100% | Balance to 100% | Balance to 100% |

Any of the above compositions is used to launder fabrics at a concentration of 10,000 ppm in water, 20-90° C., and a 5:1 water:cloth ratio. The typical pH is about 10.

Examples 11-16

Heavy Duty Liquid Laundry Detergent Compositions

|  | 11 (wt %) | 12 (wt %) | 13 (wt %) | 14 (wt %) | 15 (wt %) | 16 (wt %) |
|---|---|---|---|---|---|---|
| AES $C_{12-15}$ alkyl ethoxy (1.8) sulfate | 11 | 10 | 4 | 6.32 | 6.0 | 8.2 |
| Linear alkyl benzene sulfonate | 4 | 0 | 8 | 3.3 | 4.0 | 3.0 |
| HSAS | 0 | 5.1 | 3 | 0 | 2 | 0 |
| Sodium formate | 1.6 | 0.09 | 1.2 | 0.04 | 1.6 | 1.2 |
| Sodium hydroxide | 2.3 | 3.8 | 1.7 | 1.9 | 2.3 | 1.7 |
| Monoethanolamine | 1.4 | 1.490 | 1.0 | 0.7 | 1.35 | 1.0 |
| Diethylene glycol | 5.5 | 0.0 | 4.1 | 0.0 | 5.500 | 4.1 |
| Nonionic | 0.4 | 0.6 | 0.3 | 0.3 | 2 | 0.3 |
| Chelant | 0.15 | 0.15 | 0.11 | 0.07 | 0.15 | 0.11 |
| Citric Acid | 2.5 | 3.96 | 1.88 | 1.98 | 2.5 | 1.88 |
| $C_{12-14}$ dimethyl Amine Oxide | 0.3 | 0.73 | 0.23 | 0.37 | 0.3 | 0.225 |
| $C_{12-18}$ Fatty Acid | 0.8 | 1.9 | 0.6 | 0.99 | 0.8 | 0.6 |
| Borax | 1.43 | 1.5 | 1.1 | 0.75 | 1.43 | 1.07 |
| Ethanol | 1.54 | 1.77 | 1.15 | 0.89 | 1.54 | 1.15 |
| Ethoxylated ($EO_{15}$) tetraethylene pentaimine[1] | 0.3 | 0.33 | 0.23 | 0.17 | 0.0 | 0.0 |
| Ethoxylated hexamethylene diamine[2] | 0.8 | 0.81 | 0.6 | 0.4 | 0.0 | 0.0 |
| 1,2-Propanediol | 0.0 | 6.6 | 0.0 | 3.3 | 0.0 | 0.0 |
| Protease* | 36.4 | 36.4 | 27.3 | 18.2 | 36.4 | 27.3 |
| Mannaway ®* | 1.1 | 1.1 | 0.8 | 0.6 | 1.1 | 0.8 |
| Natalase ®* | 7.3 | 7.3 | 5.5 | 3.7 | 7.3 | 5.5 |
| Lipase†* | 10 | 3.2 | 0.5 | 3.2 | 2.4 | 3.2 |
| Liquitint ® Violet CT (active) | 0.006 | 0.002 | — | — | — | 0.002 |
| S-ACMC | — | — | 0.01 | 0.05 | 0.01 | 0.02 |
| Water, perfume, dyes & other components | Balance | Balance | Balance | Balance | Balance | Balance |

Raw Materials and Notes For Composition Examples 1-16

Linear alkylbenzenesulfonate having an average aliphatic carbon chain length $C_{11}$-$C_{12}$ supplied by Stepan, Northfield, Illinois, USA $C_{12-14}$ Dimethylhydroxyethyl ammonium chloride, supplied by Clariant GmbH, Sulzbach, Germany AE3S is $C_{12-15}$ alkyl ethoxy (3) sulfate supplied by Stepan, Northfield, Illinois, USA AE7 is $C_{12-15}$ alcohol ethoxylate, with an average degree of ethoxylation of 7, supplied by Huntsman, Salt Lake City, Utah, USA Sodium tripolyphosphate is supplied by Rhodia, Paris, France Zeolite A is supplied by Industrial Zeolite (UK) Ltd, Grays, Essex, UK 1.6R Silicate is supplied by Koma, Nestemica, Czech Republic Sodium Carbonate is supplied by Solvay, Houston, Texas, USA Polyacrylate MW 4500 is supplied by BASF, Ludwigshafen, Germany Carboxy Methyl Cellulose is Finnfix ® BDA supplied by CPKelco, Arnhem, Netherlands Savinase ®, Natalase ®, Termamyl ®, Mannaway ® supplied by Novozymes, Bagsvaerd, Denmark Lipase variant 1 to 5 described in example 5 Table 4, and combinations thereof.

Fluorescent Brightener 1 is Tinopal ® AMS, Fluorescent Brightener 2 is Tinopal ® CBS-X, Sulphonated zinc phthalocyanine and Direct Violet 9 is Pergasol ® Violet BN-Z all supplied by Ciba Specialty Chemicals, Basel, Switzerland Diethylenetriamine pentacetic acid is supplied by Dow Chemical, Midland, Michigan, USA Sodium percarbonate supplied by Solvay, Houston, Texas, USA -continued

|   | 11 (wt %) | 12 (wt %) | 13 (wt %) | 14 (wt %) | 15 (wt %) | 16 (wt %) |
|---|---|---|---|---|---|---|

Sodium perborate is supplied by Degussa, Hanau, Germany
NOBS is sodium nonanoyloxybenzenesulfonate, supplied by Eastman, Batesville, Arkansas, USA
TAED is tetraacetylethylenediamine, supplied under the Peractive ® brand name by Clariant GmbH, Sulzbach, Germany
S-ACMC is carboxymethylcellulose conjugated with C.I. Reactive Blue 19, sold by Megazyme, Wicklow, Ireland under the product name AZO-CM-CELLULOSE, product code S-ACMC.
Ultramarine Blue is supplied by Holliday Pigments, Kingston upon Hull, UK
Soil release agent is Repel-o-tex ® PF, supplied by Rhodia, Paris, France
Acrylic Acid/Maleic Acid Copolymer is molecular weight 70,000 and acrylate:maleate ratio 70:30, supplied by BASF, Ludwigshafen, Germany
Protease is FN3 supplied by Genencor International, Palo Alto, California, USA
Na salt of Ethylenediamine-N,N'-disuccinic acid, (S,S) isomer (EDDS) is supplied by Octel, Ellesmere Port, UK
Hydroxyethane di phosphonate (HEDP) is supplied by Dow Chemical, Midland, Michigan, USA
Suds suppressor agglomerate is supplied by Dow Corning, Midland, Michigan, USA
HSAS is mid-branched alkyl sulfate as disclosed in U.S. Pat. No. 6,020,303 and U.S. Pat. No. 6,060,443
$C_{12-14}$ dimethyl Amine Oxide is supplied by Procter & Gamble Chemicals, Cincinnati, Ohio, USA
Nonionic is preferably a $C_{12}C_{13}$ ethoxylate, preferably with an average degree of ethoxylation of 9.
Protease is supplied by Genencor International, Palo Alto, California, USA
Liquitint ® Violet CT is supplied by Milliken, Spartanburg, South Carolina, USA)
*Numbers quoted in mg enzyme/100 g
[1]as described in U.S. Pat. No. 4,597,898..
[2]available under the tradename LUTENSIT ® from BASF and such as those described in WO 01/05874
†Lipase described in the present specification.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A composition comprising a fabric hueing agent and a variant of a parent lipase having SEQ ID NO: 2, said variant, when compared to said parent, comprising a total of at least three substitutions, at least two of said substitutions being in Region I substitutions in the positions corresponding to the positions 231 and 233, said substitutions, other than said Region I substitutions, being selected from one or more of the following groups of substitutions:

a) at least one substitution in Region II,
b) at least one substitution in Region III, and/or
c) at least one substitution in Region IV, wherein said variant has lipase activity and the composition has improved wash performance and BR factor.

2. A detergent composition according to claim 1 wherein the lipase is further characterised in that the amino acids of the parent lipase in the positions corresponding to position 231 and 233 are substituted with an R.

3. A detergent composition according to claim 1, wherein said variant comprises a substitution in the position corresponding to position 4 of SEQ ID NO:2.

4. A detergent composition according to claim 3, wherein said substitution in the position corresponding to position 4 of SEQ ID NO:2 is V.

5. A detergent composition according to claim 1, wherein said variant comprises a substitution in the position corresponding to position 227 of SEQ ID NO:2.

6. A detergent composition according to claim 5, wherein said substitution in the position corresponding to position 227 of SEQ ID NO:2 is G.

7. A detergent composition according to claim 1, wherein the lipase is further characterised in that the at least one substitution in Region II of the parent lipase comprises substitutions selected from the group consisting of substitutions in positions corresponding to the positions 202, 211, 255 and 256.

8. A detergent composition according to claim 7, wherein the lipase is further characterised in that the at least one substitution in the parent lipase is selected from the group consisting of X202G, X211L, X255Y/V and X256K.

9. A detergent composition according to claim 1, wherein said at least one substitution in Region II comprises a substitution in the position corresponding to the position 210.

10. A detergent composition according to claim 9, wherein the position corresponding to position 210 comprises X210K.

11. A detergent composition according to claim 1, wherein the lipase is further characterised in that the at least one substitution in Region III of the parent lipase comprises substitutions selected from the group consisting of substitutions in positions corresponding to the positions 86 and 90.

12. A detergent composition according to claim 11, wherein the lipase is further characterised in that the at least one substitution in the parent lipase is selected from the group consisting of X86V and X90A/R.

13. A detergent composition according to claim 1, wherein said at least one substitution in Region III comprises a substitution in the position corresponding to the position 83.

14. A detergent composition according to claim 13, wherein the position corresponding to position 83 comprises X83T.

15. A detergent composition according to claim 1, wherein the lipase is further characterised in that the at least one substitution in Region IV of the parent lipase comprises substitutions selected from the group consisting of substitutions in positions corresponding to the positions 27, 58 and 60.

16. A detergent composition according to claims 15, wherein the lipase is further characterised in that the at least one substitution in the parent lipase is selected from the group consisting of X27R, X58N/A/G/P/T and X60S/G/N/R/K/A/L.

17. A detergent composition according to claim 1, wherein the lipase is further characterised in that the parent lipase comprises further at least one substitution outside the defined Regions I to IV.

18. A detergent composition according to claim 17, wherein the lipase is further characterised in that the at least one substitution in the parent lipase is selected from the group consisting of substitutions in positions corresponding to position 81, 147, 150 and 249.

19. A detergent composition according to claim 17, wherein the lipase is further characterised in that the at least one substitution in the parent lipase is selected from the group consisting of X81Q/E, X147M/Y, X150G and X249R/I/L.

20. A detergent composition according to claim 1, wherein the lipase is further characterised in that the parent lipase is at least 90% identical to SEQ ID NO:2.

21. A detergent composition according to claim 1 wherein the parent lipase is identical to SEQ ID NO: 2 and said variant comprises one of the following groups of substitutions:
 a) T231R+N233R+I255Y
 b) I202G+T231R+N233R
 c) I86V+L227G+T231R+N233R+P256K
 d) Q4V+S58N+V60S+T231R+N233R
 e) S58N+V60S+I90R+T231R+N233R
 f) I90A+T231R+N233R+I255V
 g) S58N+V60S+I86V+A150G+L227G+T231R+N233R+P256K
 h) S58N+V60S+L147M+F211L+T231R+N233R
 i) Q4V+S58A+V60S+S83T+I86V+A150G+E210K+L227G +T231R+N233R+P256K
 j) S58N+V60S+I86V+A150G+L227G+T231R+N233R+P256K.

22. A detergent composition according to claim 1 wherein the parent lipase is identical to SEQ ID NO: 2 and said variant comprises one of the following groups of substitutions:
 a) Q4V+S58A+V60S+S83T+I86V+A150G+E210K+L227G +T231R+N233R+P256K
 b) S58N+V60S+I86V+A150G+L227G+T231R+N233R+P256K.

23. A detergent composition according to claim 1 wherein the lipase variant is characterised in that the Benefit Risk, when measured as given in the specification, is larger than 1.

24. A detergent composition comprising a fabric hueing agent and a polypeptide having lipase activity according to claim 1 and which further has a Average Relative Performance of at least 0.8 and a Benefit Risk of at least 1.1 at the test conditions given in the specification.

25. A composition according to claim 1 comprising 0.1 to 40% anionic surfactant.

26. A composition according to claim 25, said composition being a cleaning and/or treatment composition.

27. A process of cleaning and/or treating a surface or fabric comprising the steps of optionally washing and/or rinsing said surface or fabric, contacting said surface or fabric with the composition of claim 1, then optionally washing and/or rinsing said surface or fabric.

28. A composition according to claim 1, wherein said lipase variant is a variant of SEQ ID NO: 2 comprising at least one of the mutations Q4V, S58N/A/G/P/T, I90R or Q249I/L.

* * * * *